(12) United States Patent
Raspe et al.

(10) Patent No.: US 7,691,628 B1
(45) Date of Patent: Apr. 6, 2010

(54) USE OF REV-ERB FAMILY OF RECEPTORS IN SCREENING

(75) Inventors: Eric Raspe, Mouscron (BE); Yves Bonhomme, Charbonnieres (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/720,037

(22) PCT Filed: Jun. 21, 1999

(86) PCT No.: PCT/EP99/04286

§ 371 (c)(1),
(2), (4) Date: Dec. 20, 2000

(87) PCT Pub. No.: WO99/67637

PCT Pub. Date: Dec. 29, 1999

(51) Int. Cl.
*C12N 5/06* (2006.01)
*C12P 21/06* (2006.01)
*G01N 33/53* (2006.01)

(52) U.S. Cl. .................. 435/361; 435/69.1; 435/7.8
(58) Field of Classification Search .............. None
See application file for complete search history.

(56) References Cited

U.S. PATENT DOCUMENTS 6,159,705 A * 12/2000 Trueheart et al. ............. 506/10

FOREIGN PATENT DOCUMENTS

| WO | 96 41013 | 12/1996 |
|----|----------|---------|
| WO | 97 08550 | 3/1997 |
| WO | 97 12853 | 4/1997 |
| WO | 98 52968 | 11/1998 |

OTHER PUBLICATIONS

Vu-Dac et al. 1998. J Biol Chem. 273:25713-25720.*
Fraser et al. 1997. J. Biol Chem. 1997. J Biol Chem. 272:13892-13898.*
Auwerx et al. 1996. Atherosclerosis 124 Suppl:S29-S37.*
Harding et al. 1995, Mol and Cell Biol 15:4791-4802.*
Adelmant et al 1996. PNAS 93:3553-3558.*
Terenzi et al. 1996. Prot Express. and Purif. 8:313-318.*
Forman et al. "Cross-talk among ROR alpha 1 and the Rev-erb family of orphan nuclear receptors." Molecular Endocrinology, vol. 8, 1253-1261, 1994.

* cited by examiner

*Primary Examiner*—Manjunath N Rao
*Assistant Examiner*—Shulamith H Shafer
(74) *Attorney, Agent, or Firm*—Millen, White, Zelano, Branigan, P.C.

(57) ABSTRACT

The present invention relates to the use of receptors of the Rev-erb family to screen substances which are useful in the treatment of lipid metabolism dysfunctions associated with apolipoprotein C-III. The invention relates more particularly to screening methods for selecting substances which are useful for the treatment of these dysfunctions. Lastly, the invention relates to the use of the substances thus identified for the preparation of therapeutic compositions which are useful for the treatment of lipid metabolism dysfunctions associated with apolipoprotein C-III. The subject of the present invention is also the use of screening tests for the characterization, justification and claim of the mechanism of action of substances possessing anti-atherosclerotic properties using the Rev-erb receptors and/or the response elements thereof, as well as their effect on apo C-III.

10 Claims, 13 Drawing Sheets

USE OF REV-ERB FAMILY OF RECEPTORS IN SCREENING

The present invention relates to the use of receptors of the Rev-erb family to screen substances which are useful in the treatment of lipid metabolism dysfunctions associated in particular with apolipoprotein C-III. The invention relates more particularly to screening methods for selecting substances which are useful for the treatment of these dysfunctions. Lastly, the invention relates to the use of the substances thus identified for the preparation of therapeutic compositions which are useful for the treatment of lipid metabolism dysfunctions associated with apolipoprotein C-III, such as, for example, atherosclerosis. The subject of the present invention is also the use of screening tests for the characterization, justification and claim of the mechanism of action of substances possessing anti-atherosclerotic properties using the Rev-erb receptors and/or the response elements thereof, as well as their effect on apo C-III.

Apolipoprotein C-III, referred to hereinbelow as apo C-III, is a glycoprotein of 79 amino acids synthesized in the liver and, to a lesser extent, in the intestine. It plays a major role in the metabolism of the plasma triglycerides. In point of fact, the plasma concentrations of apo C-III are positively correlated with the plasma levels of triglycerides, both in the normal population and in hypertriglyceridaemic patients (1-4). Furthermore, the relative distribution of apo C-III with respect to the other classes of lipoproteins appears to be large: an increase in the concentration of apo C-III in particles which contain apo B (apo C-III-LpB) is associated with an increased risk of cardiac or coronary diseases (5). Several lines of evidence link apo C-III with the catabolism of plasma triglycerides.

A deficiency in apo C-III is reflected by an increase in the catabolism of the very low density particles (VLDL), whereas an increase in the synthesis of apo C-III appears in hypertriglyceridaemic patients (6, 7).

Furthermore, genetic studies have revealed the relationship existing between certain polymorphisms of the apo C-III gene and high concentrations of triglycerides and of apo C-III in the plasma (8, 9).

Lastly, the overexpression of human apo C-III in transgenic animals was reflected by the development of hypertriglyceridaemia, whereas the deletion of the endogenous apo C-III gene by homologous recombination in mice led to a decrease in the plasma concentration of apo C-III and to protection of the animal against postprandial hypertriglyceridaemia (10, 11).

The results of studies carried out in vivo and in vitro indicate that apo C-III acts mainly by retarding the catabolism of triglyceride-rich particles, either by inhibiting their binding to the surface of the endothelium and the subsequent lipolysis with the lipase lipoprotein, or by interfering with the clearance of the residual particles (remnants) which is ensured by the apo E receptor (12-16).

Lastly, the importance of apo C-III in the metabolism of lipoproteins is also suggested by the observation of several characteristics of combined familial hyperlipidaemia (large amounts of VLDL and LDL associated with early cardiac and coronary diseases) in the descendants of crosses between mice whose low density particle (LDL) receptor gene has been removed by homologous recombination and mice which overexpress the human apo C-III gene (17).

The Rev-erb nuclear receptors form a subfamily of orphan nuclear receptors encoded by at least three different genes, Rev-erbα (ear1), Rev-erbβ (BD73, ear4, RVR) and HZF-2 (Rev-erbγ) (18-25), the natural ligands of which are currently unknown. The mRNA coding for the Rev-erbα nuclear receptor is expressed in many tissues, particularly in muscle, brown adipose tissue and the brain (26). Expression of the Rev-erbα gene is induced during adipocyte (26) and myocyte (53) differentiation and in the liver in response to a chronic treatment with fibrates (59). This expression also appears to follow a circadian rhythm (55). The two genes Rev-erbβ and Rev-erbγ are expressed in particular in the brain (22, 25). Rev-erbα and Rev-erbα can bind as monomers to a response element consisting of a half-site PuGGTCA preceded by an A/T-rich region of 5 base pairs (A/T-A-A/T-N-T-A/G-G-G-T-C-A (SEQ ID NO: 30)) (28, 21). A dimeric binding of Rev-erbα on a direct repetition of two AGGTCA half-sites separated by two base pairs and preceded by an A/T-rich region has also been described in vitro (29). The crystallographic structure of the complex formed from the DNA binding domain of Rev-erbα with the direct repetition of the two AGGTCA half-sites has been described (54). In contrast with what had initially been described (28), it appears that the nuclear receptors of the Rev-erb subfamily repress the transcription (29, 20). Several physiological targets of Rev-erbα have been identified to date: the oncogene N-myc (30), the rat apo A-I gene (27), the human hRev-erbα nuclear receptor itself (31) and the transcription factors myoD and myogenin (53).

The studies by the Inventors have shown that the Rev-erb receptors are negative regulators of transcription of the apo C-III gene. These receptors are thus capable of repressing the transcription of the apo C-III gene which is associated with the development of hypertriglyceridaemia and hyperlipidaemia.

The present invention thus relates to the use of Rev-erb receptors and/or one of the response elements of these receptors or a functional equivalent thereof to screen substances which are useful in the treatment of lipid metabolism dysfunctions. In addition, the present invention relates to the use of a screening process for the characterization, justification and claim of the mechanism of action of substances possessing anti-atherosclerotic properties using the Rev-erb receptors and/or the response elements thereof, as well as to their effect on apo C-III.

For the purposes of the present invention, the term "Rev-erb receptor" denotes all the α, β and γ isoforms of the Rev-erb family.

The expression "functional equivalent of Rev-erb" means any protein possessing both:

a ligand binding site having a selectivity which is comparable to that of Rev-erb for a given ligand thereof, and a DNA binding site which recognizes the same response element as Rev-erb or a response element which has a similar nucleic acid sequence.

The expression "functional equivalent of Rev-erb" also means a chimeric protein which has:

a ligand binding site having a selectivity which is comparable to that of Rev-erb for a given ligand thereof, and a DNA binding site which recognizes a response element of a reporter gene, or a protein domain which allows the ready purification of the chimera and its specific binding to defined matrices such as, for example, maltose binding protein (MBP) or glutathione-S-transferase (GST). The latter type of chimera has often been used (53). It has the advantage of allowing purification of the protein in one step by means of an affinity column or of specifically separating out this protein by means of simple procedures which are well known to those skilled in the art (coupling to beads or resins, elution with maltose or glutathione, etc.).

The expression "functional equivalent of the Rev-erb receptor response element" means any nucleic acid sequence onto which the Rev-erb receptor can bind and more particularly a sequence derived from the Rev-erb receptor response element.

The hRev-erbα receptor, the hRev-erbα messenger RNA and the hRev-erbα receptor response element are more particularly preferred in the implementation of the invention.

A subject of the present invention is thus a first type of process for screening substances which are useful in the treatment of lipid metabolism dysfunctions, which consists in placing the test substance in contact with a receptor of the Rev-erb family and/or a Rev-erb receptor response element, and/or a nuclear factor capable of functionally coupling Rev-erb to the RNA-polymerase complex, or a functional equivalent thereof, and then in measuring by any appropriate means:

the binding of the said substance to the Rev-erb receptor and/or its functional equivalent or the binding of the complex formed from the said substance and the Rev-erb receptor to its response element and/or to a nuclear factor capable of functionally coupling Rev-erb to the RNA-polymerase complex, and/or the modulation of the transcriptional activity of a gene placed under the control of a promoter comprising the said response element.

Measurement of the binding of the substance to the Rev-erb receptor and/or to its functional equivalent or the binding of the complex formed from the said substance and the Rev-erb receptor to its response element can be performed by any direct or indirect method known to those skilled in the art, such as methods using a reporter gene, binding tests, etc.

Similarly, measurement of the modulation of the transcriptional activity of a gene placed under the control of a promoter comprising the Rev-erb response element can be performed by any direct or indirect method known to those skilled in the art.

In order to specify the usefulness of the test substance in the treatment of lipid metabolism dysfunctions, the process of the invention comprises an additional step directed towards determining, by any appropriate means, the effect of the said substance on the expression of apo C-III. The determination of the effect of the test substance on the expression of apo C-III can be performed by any direct or indirect method known to those skilled in the art, such as a transfection or an mRNA analysis in vitro and on models in vitro and in vivo.

A first example of a screening process according to the present invention comprises the following steps:

a) a host cell is transfected with a DNA fragment coding for a Rev-erb receptor or a functional equivalent thereof, b) the host from step (a) is cotransfected with a construct comprising a response element of the said Rev-erb receptor and at least one reporter gene, c) the expression of the reporter gene in the presence of the test substance is measured by any appropriate means.

The response element used in step (b) may consist, for example, of the proximal fragment of the apo C-III promoter.

Any reporter gene which allows measurement of the activity of nuclear receptors on the sequence comprising their response element can be used in the screening process according to the invention. Among these, mention may be made, for example, of the chloramphenicol acetyltransferase (CAT) gene, the luciferase gene from luciole (Luc) or from *Renilla* (Ren), the secreted alkaline phosphatase (SAP) gene or the β-galactosidase (β-Gal) gene. The activity of the proteins encoded by these genes can also be easily measured by conventional methods and makes it possible to know the effect of the nuclear receptors on the expression of the genes by measuring the amount of proteins produced or their enzymatic activity.

The action of the Rev-erb receptors, and more particularly of the hRev-erbα receptor on the apo C-III gene reported by the Inventors makes it possible, of course, to use the Apo C-III gene as a reporter gene in the constructs of the invention and the screening processes using them.

In the screening process of the invention, the term "host cell" means any cell type adapted to the expression of the above genes, such as, in particular, mammalian cells, bacteria or yeasts, or alternatively insect cells. Needless to say, the vectors used are adapted to the type of cell transfected; mention may be made of plasmids, viruses or artificial chromosomes.

Another example of this first type of screening process according to the invention comprises the following steps:

a) a plasmid is created which comprises several copies of a response element recognized by Rev-erb, such as, for example, a site RevDR2 of the Rev-erbα promoter (31), the consensus site described by M. Lazar (28, 29), or the Rev-erb response element(s) identified in the apo C-III promoter. These copies of the response element are cloned upstream of a heterologous strong promoter such as the thymidine kinase promoter of the herpes simplex virus, or a homologous strong promoter such as the apo C-III promoter. This promoter is itself arranged so as to control the expression of a reporter gene such as luciferase, CAT, alkaline phosphatase or β-galactosidase, b) the construct from step (a) is transfected into cells which express Rev-erb naturally or artificially, i.e. after transient cotransfection of an expression vector or creation of a stable line which expresses Rev-erb, and c) the host from step (c) is incubated in the presence of the test substance, d) the activity of the reporter gene is measured by any appropriate means.

The revDR2 sites are Rev-erb response elements onto which the receptor binds as a dimer to modulate the transcriptional activity of the gene placed downstream. These sites can be used to sensitize a heterologous promoter to Rev-erb.

An additional example of this first type of process comprises the following steps:

a) a plasmid is created which comprises several copies of a response element recognized by Rev-erb, which are cloned upstream of a strong promoter which controls the expression of a suicide selection gene such as, for example, the activator of a toxic prodrug such as herpesvirus thymidine kinase (48), b) the construct from step (a) is transfected into a host cell, c) the host from step (b) is cotransfected using a vector which expresses Rev-erb, and d) the host from step (c) is incubated in the presence of the test substance, e) the cell survival in the presence of the toxic prodrug is measured by any appropriate means.

The toxic prodrug may be, for example, ganciclovir.

Yet another example of this first type of process comprises the following steps:

a) a plasmid is created which comprises several copies of a response element recognized by the yeast nuclear factor Gal4, which are cloned upstream of a strong promoter, such as the thymidine kinase promoter of the herpes simplex virus, which controls the activity of a reporter gene such as luciferase, CAT, alkaline phosphatase, β-galactosidase, growth hormones, etc., b) the plasmid of a chimera is created which comprises the DNA binding domain of Gal4 (49) and the DEF domains of Rev-erb which are the Rev-erb domains to which the ligands bind, c) the plasmids obtained in steps (a) and (b) are cotransfected into a host cell, and d) the host from step (c) is incubated in the presence of the test substance, e) the activity of the reporter gene is measured by any appropriate means.

The DEF domains of the nuclear receptors diverge between various members of this family. They comprise sequences involved in transactivation of the transcription and binding of the ligands and cofactors. The DEF domains of Rev-erb are combined with the Gal4 fragment which contains the first 147 amino acids of Gal4 to create a chimera Gal4-Rev-erbDEF which binds to the Gal4 response element and whose transcriptional activity depends on the Rev-erb ligands and/or cofactors (29).

The basal activity of the chimera can be increased by inserting a DNA fragment which codes for all or part of the protein VP16 (50).

The first type of screening process can also be implemented in the following way a) a plasmid is created which comprises several copies of a response element recognized by the yeast nuclear factor Gal4, which are cloned upstream of a strong promoter which controls the expression of a suicide selection gene, as explained above, b) a chimera is created which comprises the DNA binding domain of Gal4 and the DEF domains of Rev-erb, c) the plasmids obtained in steps (a) and (b) are cotransfected into a host cell, and d) the host from step (c) is incubated in the presence of the test substance, e) the cell survival in the presence of the toxic prodrug is measured by any appropriate means.

An additional example of this first type of screening process consists of the quantitative evaluation of the effects of the test compounds in systems of "double hybrid" type in yeasts or other cells which comprise the Rev-erb fragments which interact with cofactors and the corresponding fragments of the cofactors (e.g.: RIP13a, RIP13d1 (51), N-COR (52) or optionally SMRT and P300/CBP) which couple Rev-erb to the transcriptional machinery and in particular to the RNA-polymerase complex.

Another example of the first type of screening method according to the invention consists in quantitatively evaluating the effects of the test compounds on the in vitro capacity for interaction between the entire hRev-erbα protein or some of its fragments and cofactors or some of their fragments by any technique known in the prior art (for example by the CARLA approach developed for PPAR ligand screening (45), a method by measurement of the resonance fluorescence energy transfer).

A final example of the first type of screening process according to the invention consists in trans-forming a host cell as defined above, with a construct bearing a gene coding for the Rev-erb receptor or a functional equivalent thereof and/or a Rev-erb receptor response element, and then in using the said host cells or extracts thereof in "binding" tests based on the competitive displacement between a cold ligand and a labelled ligand.

A subject of the present invention is also a second type of process for screening substances which are useful in the treatment of lipid metabolism dysfunctions, which consists in determining the effect of the test substance on modulation of the expression of Rev-erb.

One example of a screening process based on measuring the modulation of the expression of Rev-erb consists in directly evaluating the effect of compounds on the cell accumulation of mRNA coding for Rev-erb by in situ hybridization (Amersham technique), RPA, quantitative or semi-quantitative RT-PCR, dot blotting or Northern blotting.

A second example of determination of the modulation of the expression of Rev-erb consists in measuring the effect of the test substance on the cell expression of the Rev-erb protein by immunocytochemistry, ELISA or Western blotting.

An additional example of this second type of process consists in indirectly evaluating the activity of the Rev-erb gene promoter. This process comprises the following steps:

a) a plasmid is created which comprises the Rev-erb gene promoter (31) cloned upstream of a reporter gene such as a luciferase, CAT, alkaline phosphatase, β-galactosidase, growth hormone, etc. gene or a selection gene such as a gene for resistance to an antibiotic or to a conversion enzyme of a non-metabolizable precursor, b) a host cell is transfected, c) the test substance is introduced, d) the activity of the reporter gene or the cell survival is measured by any appropriate means.

The Rev-erb promoter controls the expression of the Rev-erb gene and in particular contains a Rev-erb response element responsible for self-inhibition of the transcription of the gene. Constructs comprising fragments of this promoter are available to characterize the factors involved in modulation of the expression of this gene.

An additional example of a process for measuring the modulation of Rev-erb expression consists in measuring the activity of the endogenous promoter of the Rev-erb gene. This process comprises the following steps:

a) a plasmid is created which comprises several copies of a response element recognized by Rev-erb, which are cloned upstream of a strong promoter which controls the expression of a suicide selection gene such as an activator of a prodrug such as the herpesvirus thymidine kinase, or a reporter gene, b) the construct obtained in step (a) is transfected into a host cell, c) a stable cell line which expresses this construct and which expresses hRev-erbα is established, and d) the host from step (b) or (c) is incubated in the presence of the test substance, e) the cell survival in the presence of the toxic prodrug or the activity of the reporter gene is measured by any appropriate means.

A subject of the present invention is also substances selected by a screening method according to the present invention, as well as the use of these substances for the preparation of a composition, in particular a pharmaceutical composition, which represses the expression of apo C-III and is thus intended for the treatment of lipid metabolism dysfunctions in man or animals. Compounds possessing such properties are selected on the basis of their capacity to repress the expression of apo C-III, and can be ligands of Rev-erb or of Rev-erb analogues, the properties of which are demonstrated either directly from the level of expression of the apo C-III, or by means of the expression of a reporter gene, or alternatively by their capacity to form a complex with the Rev-erb receptor.

The invention thus relates more generally to the use of a substance which is capable of modulating the expression of apo C-III for the preparation of a composition, in particular a pharmaceutical composition, which is useful for the treatment and/or prevention of lipid metabolism dysfunctions associated with apolipoprotein C-III in man or animals.

More particularly, the invention relates to the use of a substance which is capable of binding to the Rev-erb receptor or to a response element thereof, for the preparation of a pharmaceutical composition which is useful for the treatment and/or prevention of lipid metabolism dysfunctions in man or animals.

The invention also relates to the use of a substance which is capable of modulating the expression of the gene coding for the Rev-erb receptor for the preparation of a composition, in particular a pharmaceutical composition, which is useful for the treatment and/or prevention of lipid metabolism dysfunctions associated with apolipoprotein C-III in man or animals.

Among the lipid metabolism dysfunctions associated with apolipoprotein C-III in man or animals, mention may be made of hyperlipidaemia, complications associated with diabetes, obesity, syndrome X, or resistance to insulin and cardiac and coronary diseases.

A subject of the present invention is also the use of a screening process as described previously in the present patent application for the characterization, justification and claim of the mechanism of action of substances possessing anti-atherosclerotic properties, using the Rev-erb receptors and/or the response elements thereof, as well as their effect on apo C-III.

Other advantages and characteristics of the invention will emerge from the examples which follow, describing the modulation of the expression of human apo C-III by the hRev-erbα receptor.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein.

I. METHODS

1. Cell Culture

Figure 1:
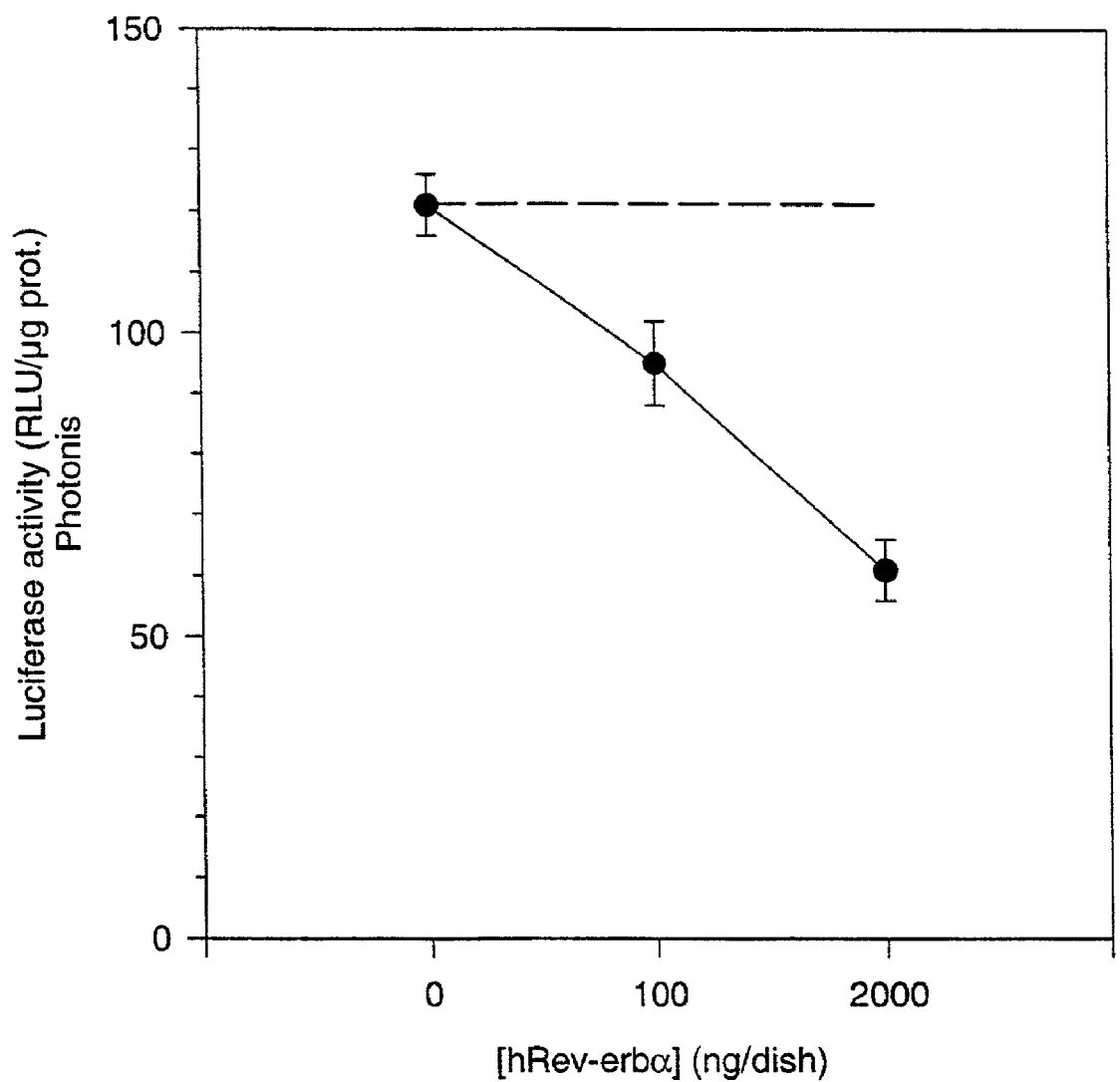
FIG. 1 shows that when HepG2 cells are cotransfected with a plasmid which comprises the fragment (−1415/+24) of the human apo C-III promoter upstream of the luciferase reporter gene (−1415/+24WThCIIILuc+) and the plasmid pSG5-hRev-erba which allows exogenous expression of the Rev-erba nuclear receptor, a 50% reduction in the activity of the reporter gene is observed.

The line HepG2 (human hepatome) is from the E.C.A.C.C. (Porton Down, Salisbury, UK), while the RK13 (rabbit kidney) cells were provided by C. Lagros (laboratory of Prof. Stéhelin). These lines were maintained under standard culture conditions (Dulbecco's modified Eagle's minimum essential medium, supplemented with 10% foetal calf serum, incubation at 37° C. in a humid atmosphere of 5% $CO_2$/95% air). The culture medium is changed every two days.

2. Construction of the Recombinant Plasmids

The activity of the promoter for the apo C-III gene was studied according to the standard techniques of the art using reporter genes. The constructs −1415/+24WT-CAT and 198/+24WT-CAT, which comprise fragments of the promoter for the human apo C-III gene which were cloned upstream of the CAT reporter gene, have been described previously (56). In order to exchange the CAT reporter gene of these constructs with the Luc+ reporter gene, the luciferase reporter gene Luc+ of the reporter vector pGL3 (Promega) was excised by the enzymes Sac I and BamH I and subcloned into the corresponding sites of the vector pBKCMV (Stratagene) to form the vector pBKCMV-Luc+. The CAT reporter gene of the construct −1415/+24WT-CAT was excised by the enzymes Kpn I and BamH I. Next, it was replaced with the Luc+ reporter gene obtained by digestion of the plasmid pBKCMV-Luc+ by the enzymes Bgl II and Kpn I to create the plasmid −1415/+24WT-Luc+. This was digested with the enzyme Pst I and self-religated to produce the construct −198/+24WT-Luc+. The plasmid −1415/+24WT-Luc+ was digested with Hind III to excise the apo C-III promoter. The DNA fragment obtained was then inserted into the Hind III site of the plasmids pGL3 (Promega) and pSL301 (Pharmacia) to create the constructs −1415/+24WTpGL3 and −1415/+24WTpSL301. The orientation of the insert was defined by sequencing. The construct −198/+24WTpGL3 was obtained by digesting the construct −1415/+24WTpGL3 with Pst I and religation. The construct −1415/+24WTpSL301 was partially digested with the enzyme Eco 0109I and self-religated to create the construct −108/+24WTpSL301. The fragment −108/+24 of the apo C-III promoter was excised from this construct by the enzymes Xma I and Hind III and cloned into the corresponding sites of the vector pGL3 to create the construct −108/+24WTpGL3. The fragment −82/+24 of the human apo C-III promoter was amplified by PCR using the construct −1415/+24pGL3 as matrix by means of the primers hCIIIF33 and 512. The product obtained was digested with the enzymes Sac I and Hind III and cloned into the corresponding sites of the plasmid pGL3 to give the construct −82/+24WTpGL3. To produce the construct −64/+24WTpGL3, the construct −1415/+24pGL3 was digested exhaustively with the enzyme BstX I, made blunt by treatment with the Klenow fragment of DNA polymerase, digested with the enzyme Sma I and self-religated. To create the construct −62/+24WTpGL3, the construct −1415/+24WTpSL301 was digested exhaustively by the enzyme Eco 0109I, made blunt by treatment with the Klenow fragment of DNA polymerase and self-religated. The fragment −62/+24 of the apo C-III promoter was then excised from this construct with the enzymes Xma I and Hind III and cloned into the corresponding sites of the vector pGL3. The point mutants of the apo C-III promoter −1415/+24TaTaKOpGL3, −198/+24TaTaKOpGL3 and −82/+24TaTaKOpGL3 were obtained using the "quick change site directed mutagenesis kit" (Stratagene) according to the manufacturer's instructions, using the oligonucleotides hCIIIF29/hCIIIR29 and the corresponding wild-type constructs as matrix.

Table 1 collates the sequences of the oligo-nucleotides used (SEQ ID NOS 1-29, respectively, in order of appearance).

| Name | Sequence | 5' end | 3' end | Use | Comments |
|---|---|---|---|---|---|
| hCIIIR29 | 5'-CAGGCAGGAGGGTTCATGTGTGTTTTATATCATCTCC-3' | −3 | −39 | mutagenesis | −22, −21, −20, −19, −18 |
| hCIIIF33 | 5'-CCCTCATCTCCACTGGTGAGCTCGTG-3' | −106 | −81 | cloning | + site Sac I |
| hCIIIF34 | 5'-GATCCGATAAAACAGGTCAGAA-3' | −33 | −15 | cloning, gel shift | + site BamH I 22, −21, −20, −19, −18, mutated |
| hCIIIR34 | 5'-GATCTTCTGACCTGTTTTATCG-3' | −15 | −34 | cloning, gel shift | + site Bgl II 22, −21, −20, −19, −18, mutated |
| hCIIIF35 | 5'-GATCCGATAAAACACACATGAA-3' | −33 | −15 | cloning, gel shift | + site BamH I |
| hCIIIR35 | 5'-GATCTTCATGTGTGTTTTATCG-3' | −15 | −34 | cloning, gel shift | + site Bgl II |
| hCIIIF36 | 5'-GATCCCGCTGGGCAAAGGTCACCTGCA-3' | −67 | −90 | cloning, gel shift | + site BamH I |
| hCIIIR36 | 5'-GATCTGCAGGTGACCTTTGCCCAGCGC-3' | −90 | −67 | cloning, gel shift | + site Bgl II |
| hCIIIF38 | 5'-GATCCTCACCTGCTGACCAGTGGAGA-3' | −80 | −100 | cloning, gel shift | + site BamH I |
| hCIIIR38 | 5'-GATCTCTCCACTGGTCAGCAGGTGAG-3' | −100 | −80 | cloning, gel shift | + site Bgl II |
| 82 | 5'-GATGGGATCCGCCAGGGTTTTCCCAGTCACGAC-3' | 4232 | 4282 | cloning | pBLCAT4 |
| 510 | 5'-TCGCCAAGCTTCTCGTGATCTGCGGCA-3' | 215 | 189 | cloning | + site Hind III; pBLCAT4 |
| 512 | 5'-TATGCAGTTGCTCTCCAGCGGTTCCATCTTCC-3' | 169 | 138 | cloning | pGL3 |
| 514 | 5'-CGACTCTAGAAGATCTTGCCCCGCCCAGCG-3' | 21 | 50 | cloning | pBLCAT4 |
| 1129 | 5'-GATCCGGAAAAGTGTGTCACTGGGGCACGA-3' | | | cloning, gel shift | + site BamH I |
| 1142 | 5'-GATCTCGTGCCCCAGTGACACACTTTTCCG-3' | | | cloning, gel shift | + site Bgl II |
| hCIIIF6a | 5'-*GATCC*TCATCTCCACTGGTCAGCAGGTGACCTTTGC-3' | −104 | −72 | gel shift | |
| hCIIIR6a | 5'-*GATC*GGCAAAGGTCACCTGCTGACCAGTGGAGATGAG- | −72 | −104 | gel shift | |

-continued

| Name | Sequence | 5' end | 3' end | Use | Comments |
|---|---|---|---|---|---|
| | 3' | | | | |
| hCIIIF8 | 5'-GATCTGATATAAAACAGGTCAGAACCCTC-3' | -34 | -10 | gel shift | |
| hCIIIR8 | 5'-GATCGAGGGTTCTGACCTGTTTTATATCA-3' | -10 | -34 | gel shift | |
| hCIIIF12 | 5'-GATCGATATAAAACAGGCAGGAACCCTC-3' | -33 | -10 | gel shift | -20, -19, -18 mutated |
| hCIIIR12 | 5'-GATCGAGGGTTCCTGCCTGTTTTATATC-3' | -10 | -33 | gel shift | -20, -19, -18 mutated |
| hCIIIF15 | 5'-GATCCTCAGTGCCTGCTGCCCTGGAGATGATATAA-3' | -56 | -27 | cloning, gel shift | + site BamH I |
| hCIIIR15 | 5'-GATCTTATATCATCTCCAGGGCAGCAGGCACTGAG-3' | -27 | -56 | cloning, gel shift | + site Bgl II |
| hCIIIF17 | 5'-GATCCTTGCCCAGCGCCCTGGGTCCTCAGTGCCTGA-3' | -76 | -47 | cloning, gel shift | + site BamH I |
| hCIIIR17 | 5'-GATCTCAGGCACTGAGGACCCAGGGCGCTGGGCAAG-3' | -47 | -76 | cloning, gel shift | + site Bgl II |
| hCIIIF21 | 5'-GATCTCATCTCCACTGGTCAGCAGGTGACCTTTGCCCAGCGCCCTG-3' | -102 | -62 | cloning, gel shift | + site Bgl II |
| hCIIIR21 | 5'-GATCCAGGGCGCTGGGCAAAGGTCACCTGCTGACCAGTGGAGATGA-3' | -62 | -102 | cloning, gel shift | + site BamH I |
| hCIIIF29 | 5'-GGAGATGATATAAAACACACATGAACCCTCCTGCCTG-3' | -39 | -3 | mutagensis | -22, -21, -20, -19, -18 |

The plasmid Tk-Luc+ was constructed by inserting the Luc+ reporter gene, obtained by digesting the plasmid pBKCMV-Luc+ with the enzymes Bgl II and Kpn I, into the vector pBLCAT4 (32) cleaved with Bgl II and Kpn I, in place of the CAT reporter gene. The construct (RevDR2)$_{3x}$TkLuc+ (given as RevDR2TkLuc+ in FIG. 12b) was obtained by exchanging the CAT reporter gene of the corresponding construct with the Luc+ reporter gene (Bgl II/EcoR I digestion). The corresponding CAT construct was obtained by the strategy described previously (57) using the oligonucleotides 1129 and 1142 (Table 1). The plasmid pTkpGL3 was constructed by PCR amplification of the fragment of the thymidine kinase promoter of the herpes simplex virus which is present in the plasmid pBLCAT4, using the primers 514 and 510 (Table 1). The PCR fragment obtained was then digested with the enzymes Bgl II and Hind III and inserted into the corresponding sites of the vector pGL3. The constructs (−58/−27)$_{8x}$TkpGL3 and (−47/−79)$_{1x}$TkpGL3 were obtained according to the strategy described previously (57) using the oligonucleotides hCIIIF15/hCIIIR15 and hCIIIF17/hCIIIR17, respectively. The intermediate constructs in the vector pic20H were digested with the enzymes Sal I and Xho I. The inserts obtained were then cloned into the Xho I site of the vector TkpGL3 and their orientation defined by sequencing. In order to insert, in a single step, several oriented copies of DNA fragments liable to contain the elements of response to the nuclear receptors studied according to the strategy described previously (57), the construct pTkpGL3 was digested with the enzyme BamH I, made blunt by treatment with the Klenow fragment of DNA polymerase and self-religated (vector TkpGL3BKO). The constructs (−33/−16)$_{3x}$TkpGL3, (−33/−16TaTaKO)$_{3x}$TkpGL3, (−109/−62)$_{1x}$TkpGL3, (−100/−80)$_{3x}$TkpGL3, (−87/−67)$_{3x}$TkpGL3 and (−87/−67C3P3'KO)$_{3x}$TkpGL3 were obtained by cloning into the vector TkpGL3BKO, according to the strategy described previously (57), using the oligonucleotides hCIIIF34 and hCIIIR34, hCIIIF35 and hCIIIR35, hCIIIF21 and hCIIIR21, hCIIIF38 and hCIIIR38, hCIIIF36 and hCIIIR36, hCIIIF37 and hCIIIR37, respectively. The plasmid pG5TkpGL3 was obtained by inserting 5 copies of the response element of the yeast transcription factor Gal4 (site 17 m) (49) upstream of the Tk promoter in the plasmid TkpGL3.

The plasmids pSG5-hHNF4, pSG5-hRev-erbα, pSG5-cRev-erbβ and pCMX-hRORα1, allowing the exogenous expression of the corresponding nuclear receptors, being obtained as described previously (25, 31, 34, 35). The plasmid pGal4-ɸ was constructed by subcloning the DNA binding domain of the yeast transcription factor Gal4 present in the plasmid pBD-Gal4 (Stratagene) into the Hind III and EcoR I sites of the vector pCDNA3. In order to generate the plasmid pBDGal4-hRev-erbαDEF, the plasmid pSG5-hRev-erbα was cleaved with the enzymes Xho I and BamH I and cloned into the corresponding sites of the vector pBKCMV. The plasmid thus obtained was then digested with the enzyme Xho I, made blunt by treatment with the Klenow fragment of DNA polymerase and digested with the enzyme Spe I. This insert was then cloned into the vector pGal4-ɸ prerestricted with EcoR I, made blunt by treatment with the Klenow fragment of DNA polymerase and digested with Xba I to create the plasmid pGal4-hRev-erbαDEF. All the constructs were confirmed by sequencing.

3. Transient Transfection and Measurement of Activity of the Human apo C-III Promoter The activity of the nuclear receptors was measured by standard techniques of reporter gene/cotransfection. The DNA was introduced into the cells studied by the common techniques available in the laboratory (calcium phosphate, electroporation, lipofection, etc.). The vectors pSG5, pCNA3 and pCMX were used as negative controls. In the experiments performed using the technique of precipitation with calcium phosphate, the cells plated out in 60 mm culture dishes were transfected at 50-60% confluence with a plasmid mixture which generally comprised, in addition to the reporter plasmids CAT, Luc+ or pGL3 (0.5 μg/60 mm dish) and the expression vectors pSG5-hRev-erbα, pCMX-hRORα1 and pSG5-hHNF4 (0.1-1 μg/60 mm dish), 0.1 μg/60 mm dish of pCMV-β-gal plasmid (Clontech) used as a control of the transfection efficacy (36). After 5 to 6 hours, the cells were washed twice with a washing buffer (0.15 M NaCl, 0.01 M sodium phosphate, pH 7.2) and incubated for 36 hours in fresh culture medium containing 10% foetal calf serum. After transfection, the cells were lysed and the luciferase and β-galactosidase activities were measured according to standard protocols (37). For the experiments performed by lipofection, the cells were plated out in 24-well dishes at a rate of 10,000 cells per well and incubated for 16 hours at 37° C. before transfection. The cells were then transfected for two hours at 37° C. in a serum-free culture medium using a cationic lipid. The plasmids (reporter vectors: 50 ng/well; expression vectors: 100 ng/well, transfection-efficacy control vectors: pSV-βgal (Promega) (50 ng/well) and DNA entrainer (pBluescript (Stratagene) added to bring the amount of DNA transfected to 500 ng/well) were dissolved in serum-free DMEM supplemented with NaCl (150 mM), sodium bicarbonate (50 mM) and cationic lipid (6 nmol/μg DNA), spun down, incubated for 30 minutes at room temperature and added to the cells. After incubation for two hours, the cells were rinsed with the washing buffer described above and incubated for 36 hours in fresh culture medium containing 10% foetal calf serum. After the experiment, the cells were rinsed with washing buffer and the luciferase activity was measured using the "Dual-Luciferase™ Reporter Assay System" kit from Promega according to the manufacturer's instructions. The protein content of the extracts obtained was assayed by the Bradford technique using the "Bio-Rad Protein Assay" kit (Bio-Rad).

4. Gel Retardations

The protein hRev-erbα was synthesized in vitro from the plasmid psG5-hRev-erbα by the reticulocyte lysate technique using the kit "TnT T7 quick coupled transcription/translation system" from Promega. The gel retardation experiments were carried out according to the protocol described previously (43, 44, 46) using oligonucleotides used to synthesize the double-stranded DNAs used as probes, which are described in Table 2.

TABLE 2

| Name | Sense oligonucleotide | Antisense oligonucleotide |
|---|---|---|
| HCIII-TaTaWT | hCIIIF8 | hCIIIR8 |
| HCIII-TaTaKO | hCIIIF12 | hCIIIR12 |
| C3P-DR2 | hCIIIF6a | hCIIIR6a |
| Rev-DR2 | 1129 | 1142 |

The double-stranded oligonucleotides were obtained by incubating 2.5 or 5 μg of the sense and antisense oligonucleotides diluted in a hybridization buffer (50 mM Tris-HCl pH 8, 50 mM KCl, 5 mM $MgCl_2$, 10 mM DTT) at 100° C. for 10 min and then at 65° C. for 10 min and by cooling the mixture slowly to room temperature.

The binding buffer had the following composition:

10 mM Hepes, 80 mM KCl, 5% glycerol, 10 mM DTT, 0.1 μg/μl polydIdC, 50 ng/μl herring sperm DNA, 1 μg/μl bovine serum albumin, reticulocyte lysate: 10%.

5. Animal Models

The mice whose Rev-erbα gene has been destroyed by homologous recombination (Rev-erbα KO) were obtained by the team directed by Björn Vennström (Laboratory of Developmental Biology, CMB, Karolinska Institute, Stockholm, Sweden) (SV1290laHsd background crossed with a BalbC background) (Chomez, P., Neveu, I., Mansén, A., Keisler, E., Larsson, L., Vennström, B., Arenas, E., submitted for publication). Björn Vennström provided us with blood samples and liver samples from (−/−) or wild-type (+/+) Rev-erbα KO transgenic mice subjected to a Chow diet. The blood and tissues were collected after fasting for 4 hours. The blood was taken from the caudal vein and the serum recovered after centrifugation at 4° C. for 25 minutes at 12,000 revolutions/minute, stored at 4° C. and used to analyse the lipid parameters, the lipoproteins and the apolipoproteins. After anaesthesia with $CO_2$, the mice were sacrificed and the tissue samples taken, frozen in liquid nitrogen and stored at −80° C. for RNA analysis.

6. Analysis of the Lipid Parameters, Lipoproteins and Apolipoproteins

The serum lipids and apolipoproteins were determined by enzymatic tests adapted for microtitration plates using commercially available reagents. The levels of apo C-III in the serum were measured by immunonephelemetry using polyclonal antibodies produced in the laboratory of Prof. Fruchart. The cholesterol and triglyceride profiles of the lipoproteins were obtained by "Fast Protein Liquid Chromatography" (FPLC). The serum lipoproteins (200 μl pool of serum representative of the average) were separated by exclusion chromatography using a Superose 6HR 10/30 column (Pharmacia) at a constant flow rate (0.2 ml/minute of a phosphate buffer (10 mM, pH 7.4) supplemented with 0.01% EDTA and 0.01% $NaN_3$). The optical density of the effluent was measured at 280 nm. 0.27 ml fractions were collected and the total amounts of cholesterol and triglycerides present in these fractions were measured.

The extractions of hepatic RNA from transgenic mice, the preparation and hybridization of the Northern and dot blots and the measurement of the apo C-III mRNA levels were carried out according to the protocols described previously (38). The cDNAs of the clone 36B4 coding for human PO acidic ribosomal phosphoprotein (39), GAPDH (40), β-actin (41) or rat apo C-III (38) were used as control. The cDNA probes were labelled with $^{32}P$ using random primers by means of the kit supplied by Boehringer Mannheim. The membranes were hybridized with $1.5 \times 10^6$ cpm/ml of each probe according to the protocol described previously (42). They were washed once with 0.5×SSC buffer and 0.1% SDS at room temperature for 10 minutes and twice in the same buffer at 65° C. for 30 minutes and then autoradiographed (X-OMAT-AR film, Kodak). The autoradiographs were analysed by densitometry (Biorad GS670 densitometer). The results were standardized relative to the levels of the mRNAs of the control probes used (42).

II. RESULTS

Figure 2:
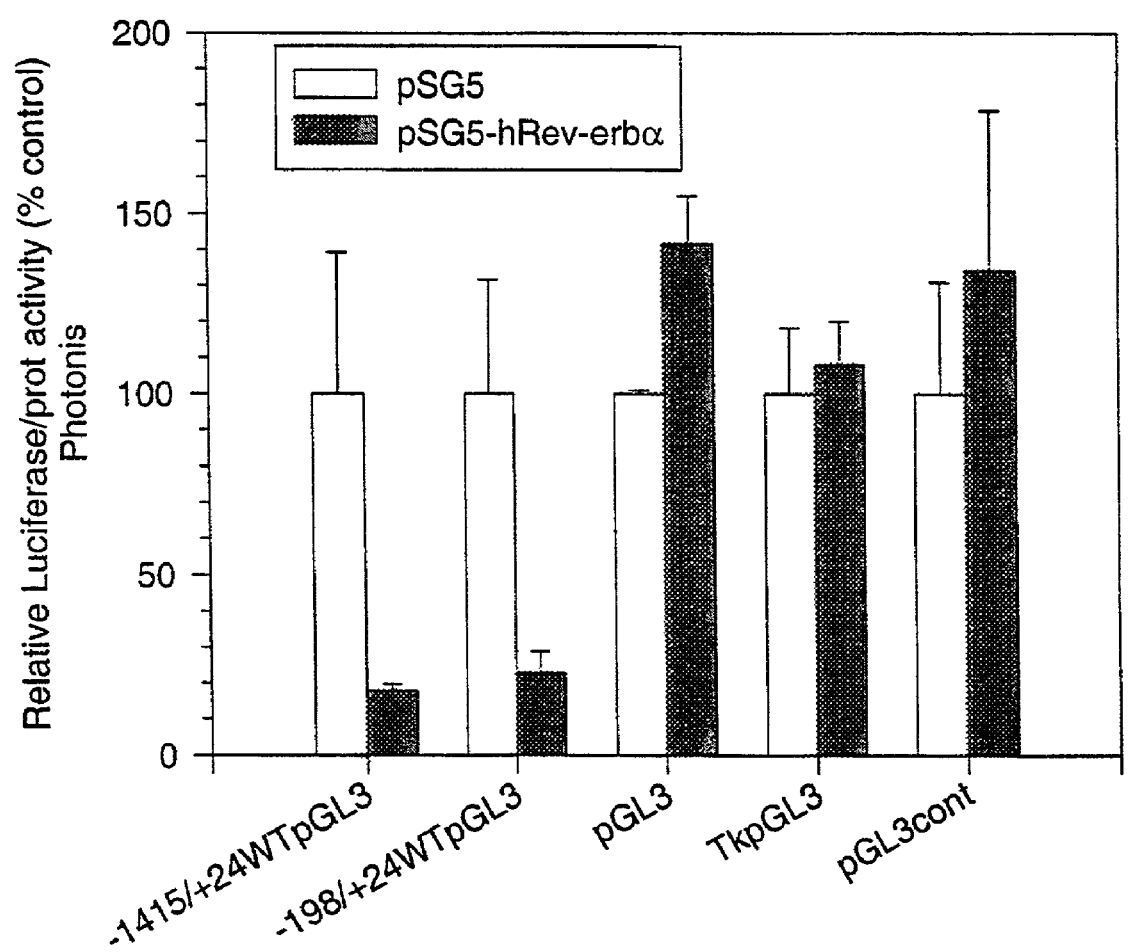
FIG. 2 shows that the activity of two heterologous promoters, the promoter for the thymidine kinase gene of the herpes simplex virus (noted as TkpGL3), or the major late promoter of the SV40 virus (noted as pGL3), is also insensitive to the action of hRev-erbα. The effect of this nuclear receptor on the promoter for the human apo C-III gene is thus specific.
Figure 3:
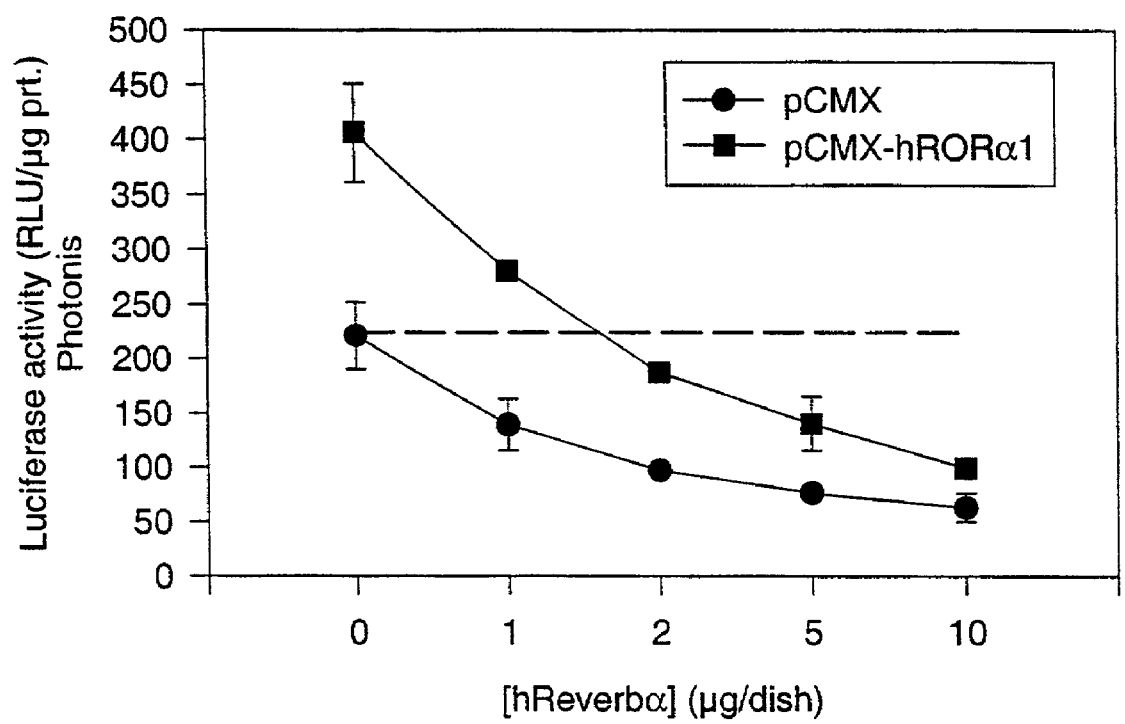
FIGS. 3 and 4 show that irrespective of the nuclear receptor cotransfected, hRev-erba reduces the activity of the reporter gene and that the effect of hRev-erba is dominant.
Figure 4:
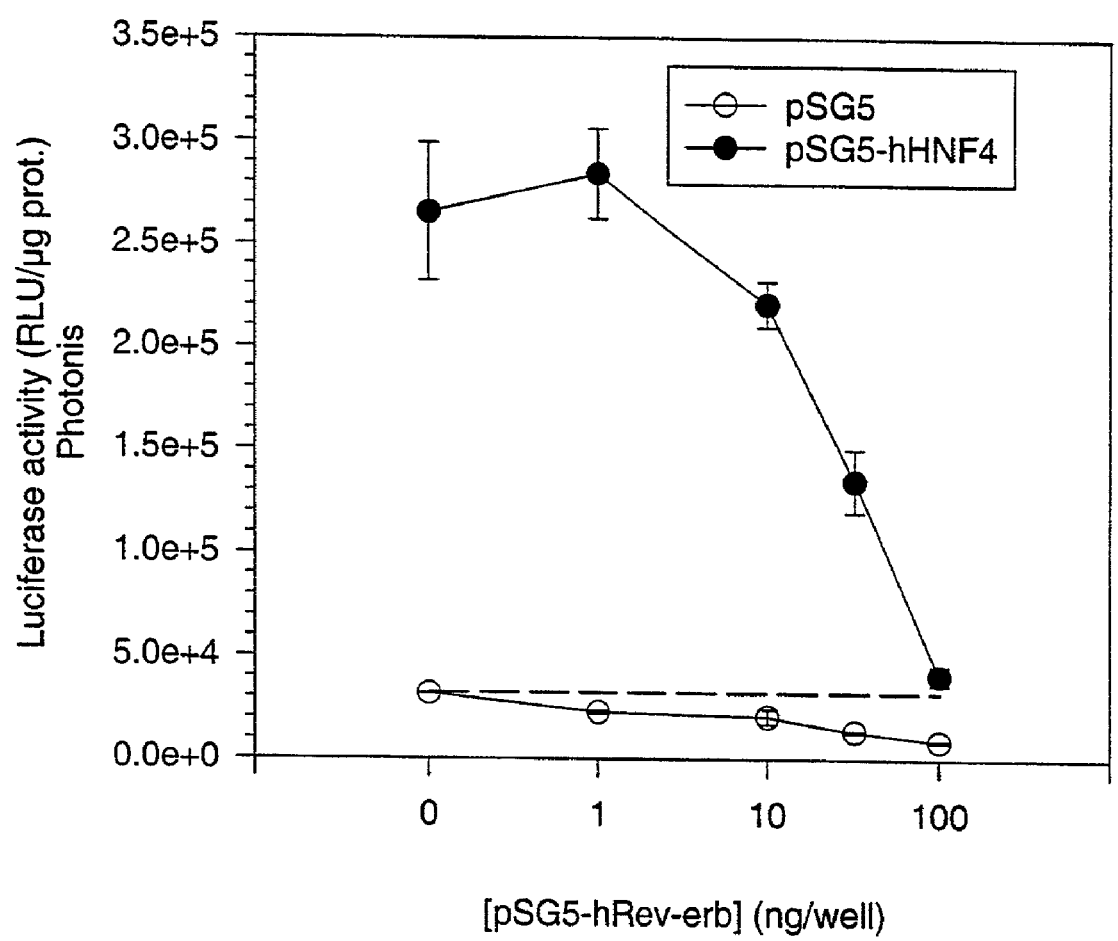

1. hRev-erbα Represses the Activity of the Human apo C-III Promoter in HepG2 and RK13 Cells When HepG2 cells are cotransfected with a plasmid which comprises the fragment (−1415/+24) of the human apo C-III promoter upstream of the luciferase reporter gene (−1415/+24WThCIIILuc+) and the plasmid pSG5-hRev-erbα which allows exogenous expression of the Rev-erbα nuclear receptor, a 50% reduction in the activity of the reporter gene is observed (FIG. 1). Similar results are obtained when RK13 (rabbit kidney) cells are cotransfected with these same constructs (FIGS. 2, 3). This model, whose phenotype is more stable than that of the HepG2 cells, will be preferred for the characterization of the effect of hRev-erbα and of its isoforms. In addition, the effect of hRev-erbα depends on the amount of expression vector transfected (FIGS. 1, 3 and 4) and is independent of the transfection protocol used (precipitation of the DNA with calcium phosphate (FIGS. 1 to 3) or lipofection (FIG. 4 and subsequent figures). Since the transfection efficacy by the second method is higher, since the amounts of DNA used can be greatly reduced and since the transfection can be carried out in the presence of an excess of inert entraining DNA, the latter method is preferred. Lastly, the effect of hRev-erbα on the activity of the fragment −1415/+24 of the human apo C-III promoter is also observed with other reporter genes (e.g. CAT) (data not illustrated), with reporter plasmids whose skeletons differ, such as pBL-CAT5 (FIGS. 1 and 3) or pGL3 (FIGS. 2, 4 and subsequent figures) or with other expression vectors such as pCDNA3 (data not illustrated): the effect of hRev-erbα is robust. The vector pGL3, which is widely used in the art, is preferred for the study hereinbelow.

These results suggest the presence of a response element to the hRev-erbα nuclear receptor in the human apo C-III promoter which is capable of reducing the activity of this promoter.

2. The Effect of hRev-erbα is Specific

FIG. 2 shows that the activity of the reporter gene for the vector lacking promoter (pGL3) is not affected by the exogenous expression of hRev-erbα. Furthermore, the activity of two heterologous promoters, the promoter for the thymidine kinase gene of the herpes simplex virus (noted as TkpGL3 in FIG. 2), or the major late promoter of the SV40 virus (noted as pGL3 in FIG. 2), is also insensitive to the action of hRev-erbα. The effect of this nuclear receptor on the promoter for the human apo C-III gene is thus specific.

3. The Effect of hRev-erbα is Dominant

Several members of the superfamily of nuclear hormone receptors to which hRev-erbα belongs recognize response elements which are specific to the level of the human apo C-III promoter: HNF4, the complex PPAR/RXR, COUPTF-I and COUPTF-II bind to the site C3P (−82/−70) (47, 60, 61, 62) and modulate the activity of the human apo C-III promoter. In addition, we have observed that the nuclear receptor hRORα increases the activity of this promoter partly via the site C3P (−82/−70) (unpublished data forming the subject of the filing of an independent PCT patent (PCT/EU99/02001)). In order to establish the extent to which hRev-erbα influences the action of other nuclear hormone receptors, RK13 cells were cotransfected with a fixed amount of reporter plasmid and plasmids allowing the exogenous expression of the hHNF4 or hRORα receptors and increasing amounts of plasmid allowing the exogenous expression of hRev-erbα. Irrespective of the nuclear receptor cotransfected, hRev-erbα reduces the activity of the reporter gene: the effect of hRev-erbα is dominant (FIGS. 3 and 4).

4. Identification of the Molecular Site of Action of hRev-erbα a. Analysis of the Deletion Mutants of the Human apo C-III Promoter

Figure 5:
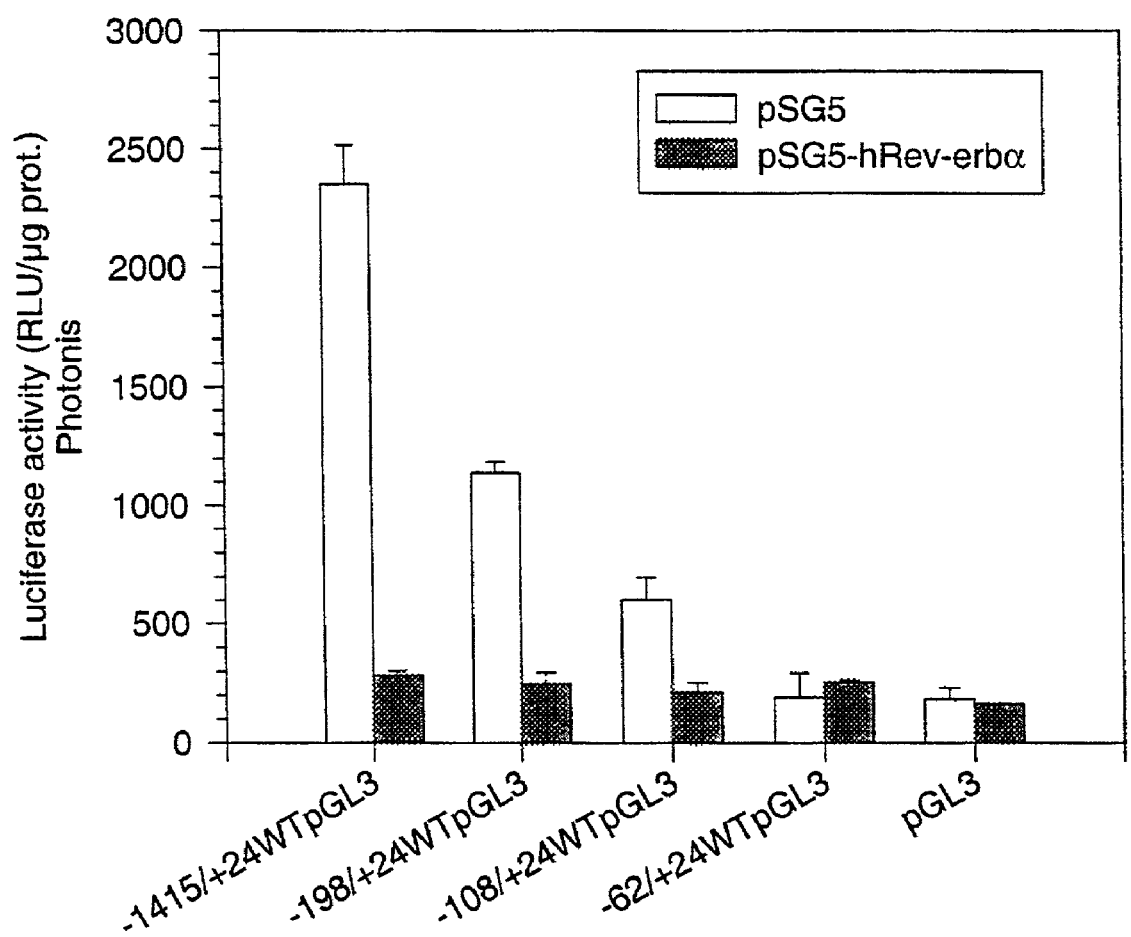
FIG. 5 shows that the activity of the reporter gene decreases when the apo C-III promoter cloned upstream of it is gradually truncated. The activity of the promoter is lost between positions −108 and −62.

FIG. 5 shows a decrease in the activity of the reporter gene when the apo C-III promoter cloned upstream of it is gradually truncated. The activity of the promoter is lost between positions −108 and −62. This region comprises the site C3P (−82/−70) whose importance in controlling the activity of the apo C-III promoter is known in the prior art (56, 60 and 62). In the experiments presented, the fragment −1415/+24 of the apo C-III promoter amplifies the activity of the Luc+ reporter gene of the plasmid pGL3 by a factor of 10. The exogenous expression of hRev-erbα reduces this activity to a level close to that of the pGL3 vector lacking promoter: the effect of hRev-erbα is powerful. It is clearly observed up to the deletion −108/+24. The results obtained with construct −62/+24 are difficult to interpret: the activity of the reporter gene is often close to that observed with the reporter pGL3, probably due to the absence of the C3P site. These results indicate the presence of at least one site of action of hRev-erbα in the portion of the human apo C-III promoter included between positions −108 and +24.

Figure 6:
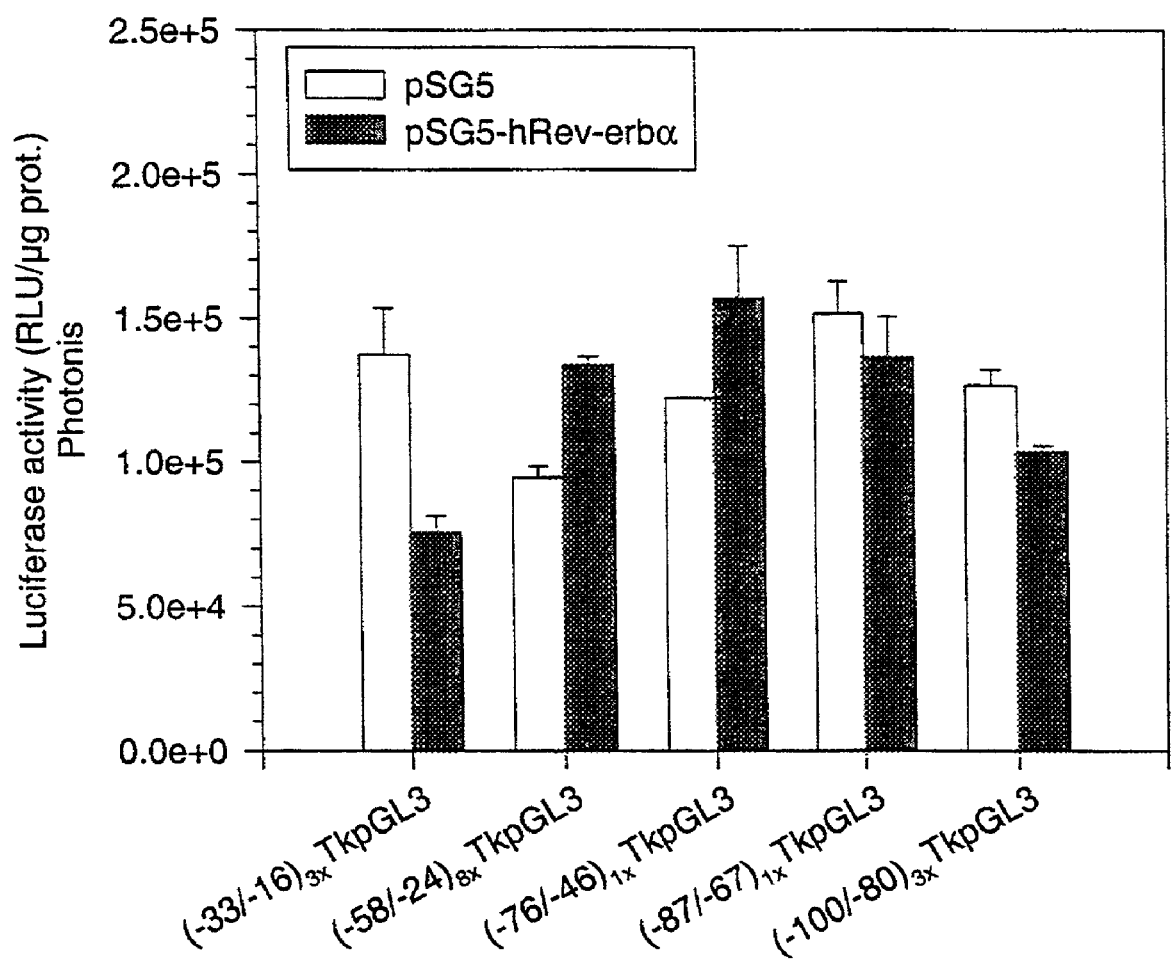
FIG. 6 shows that the activity of the construct (−33/−16) 3XTKpGL3 is reduced by hRev-erba.

In order to localize the hRev-erbα response element(s) present in this region of the apo C-III promoter, fragments overlapping this region (positions −33/−16, −58/−24, −76/−46, −87/−67 and −100/−80) were cloned into one or more oriented copies upstream of the TK promoter. FIG. 6 shows that the activity of the construct $(-33/-16)_{3X}$TkpGL3 is reduced by hRev-erbα. The weak repression of the construct (−100/−80)3xTkpGL3 described in FIG. 6 is not observed in all the experiments.

b. Analysis of the Promoter by Gel Retardation

In order to identify the portions of the apo C-III promoter to which the hRev-erbα protein binds, overlapping double-stranded oligonucleotides were phosphorylated in the presence of ATP-$\gamma^{32}$P and incubated with the hRev-erbα protein synthesized in vitro (rabbit reticulocyte lysate programmed using the plasmid pSG5-hRev-erbα or with the unprogrammed lysate). The DNA/protein complexes thus obtained were then resolved on polyacrylamide gel (gel retardation method). Two specific hRev-erbα complexes were identified on the Rev-DR2 response element present on the promoter for the hRev-erbα gene used as reference.

Figure 7:
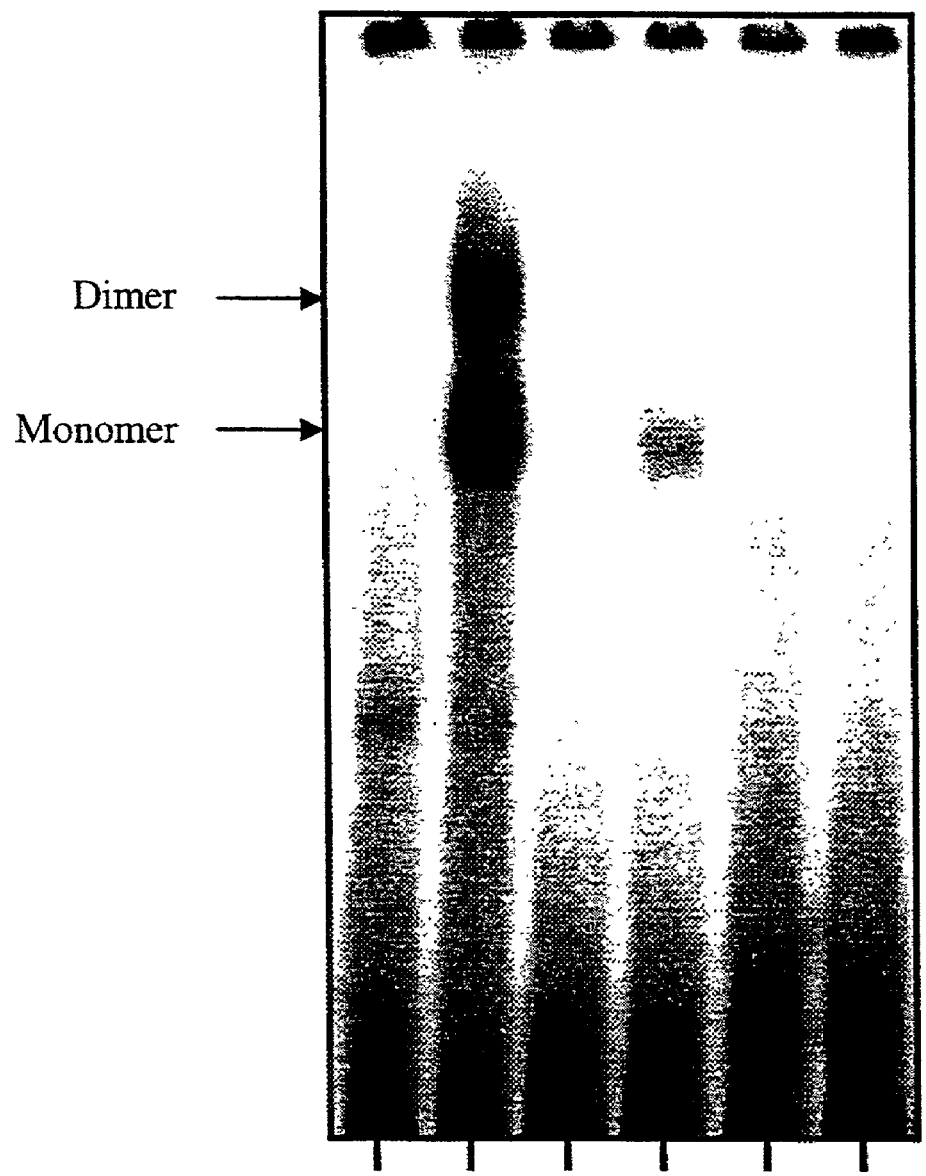
FIG. 7 shows results of gel retardation experiments with labelled oligonucleotides which cover other fragments of the portion between the positions −198 and +24 of the promoter for the human apo C-III gene (for example with the double-stranded oligonucleotide corresponding to the fragment −104/−72 ("C3P-DR2") of the apo C-III promoter.

These complexes correspond to binding of the hRev-erbα receptor as a monomer or dimer to the response element (31). A specific hRev-erbα complex was identified on the fragment −34/−10 of the promoter for the human apo C-III gene and is marked with an arrow in FIG. 7. This complex migrates to a molecular weight equivalent to that of the monomeric complex of hRev-erbα with the Rev-DR2 response element. The intensity of the hRev-erbα/(−34/−10) complex observed is weaker than that of the hRev-erb/(Rev-DR2) complex, which indicates lower affinity of the site (−34/−10) for hRev-erbα. Analysis of the sequence of the fragment −34/−10 shows the presence of a perfect AGGTCA half-site preceded by an A/T-rich region in position −23/−18. However, the base located in position −1 relative to this half-site is a C, which differs from the consensus defined by the art. This difference may explain the low affinity of the site for hRev-erbα. The corresponding double-stranded oligonucleotide whose −23/−18 site sequence is mutated (AGGTCA→AGGCAG) (hCII-ITaTamut) does not form a complex with the hRev-erbα protein (data not illustrated). Finally, we observed no significant gel retardations with labelled oligonucleotides which cover other fragments of the portion between the positions −198 and +24 of the promoter for the human apo C-III gene (for example with the double-stranded oligonucleotide corresponding to the fragment −104/−72 ("C3P-DR2") of the apo C-III promoter (FIG. 7).

In conclusion, the gel retardation experiments identified the AGGTCA half-site present in position −23/−18 of the promoter for human apo C-III as a probable hRev-erbα response element.

c. Analysis of the Point Mutants of the Promoter for the Human Apo C-III Gene

Figure 8:
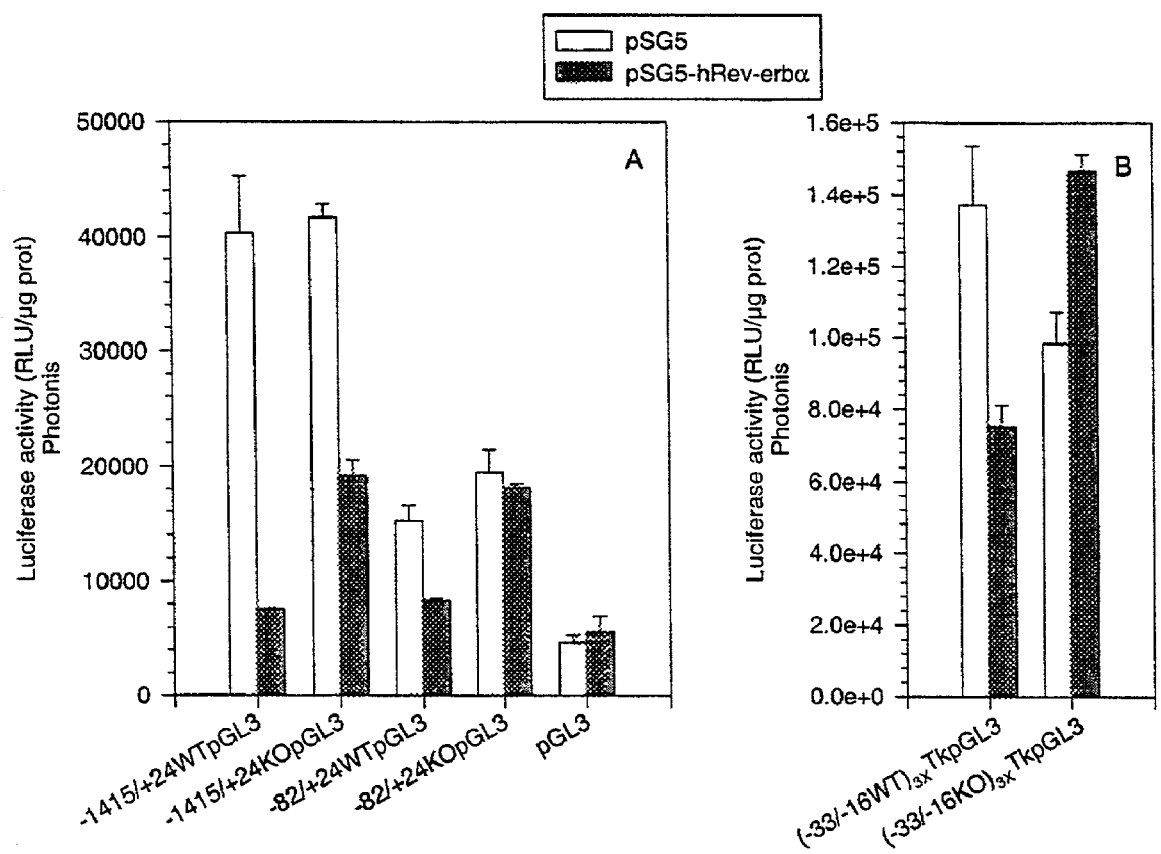
FIG. 8A indicates that the mutation of the AGGTCA half-site present in position (−23/−18) of the human apo C-III promoter reduces the sensitivity of the entire promoter to hRev-erba by 50%. The effect of hRev-erba is totally lost when the construct −82/+24WTpGL3 is mutated.
FIG. 8B shows that mutation of the −23/−18 site in the construct (−33/−16WT) 3xTkpGL3 (to give the construct 33/−16KO) 3XTkpGL3) suppresses its sensitivity to hRev-erba.

In order to validate the results obtained with the deletion mutants and with the gel retardation technique, the constructs −1415/+24WTpGL3 and −82/+24WTpGL3 were mutated by site-directed mutagenesis on the AGGTCA half-site present downstream of the TaTa box of the apo C-III gene (−23/−18). Moreover, we cloned, upstream of the Tk promoter, three copies of the −33/−16 fragment of the human apo C-III promoter whose AGGTCA site was modified in accordance with the mutations of the constructs −1415/+24WTpGL3 and −82/+24WTpGL3. FIG. 8A indicates that the mutation of the AGGTCA half-site present in position (−23/−18) of the human apo C-III promoter reduces the sensitivity of the entire promoter to hRev-erbα by 50%. The effect of hRev-erbα is totally lost when the construct −82/+24WTpGL3 is mutated. Similarly, mutation of the −23/−18 site in the construct (−33/−16WT)$_{3x}$TkpGL3 (to give the construct (−33/−16KO)$_{3x}$TkpGL3) suppresses its sensitivity to hRev-erbα (FIG. 8B).

d. Conclusions

At least one site involved in the action of hRev-erbα on the promoter for the human apo C-III gene has been clearly identified: the AGGTCA half-site located in position −23/−18 of the apo C-III promoter.

5. Effects of the hRev-erbα Isoforms

Figure 9:
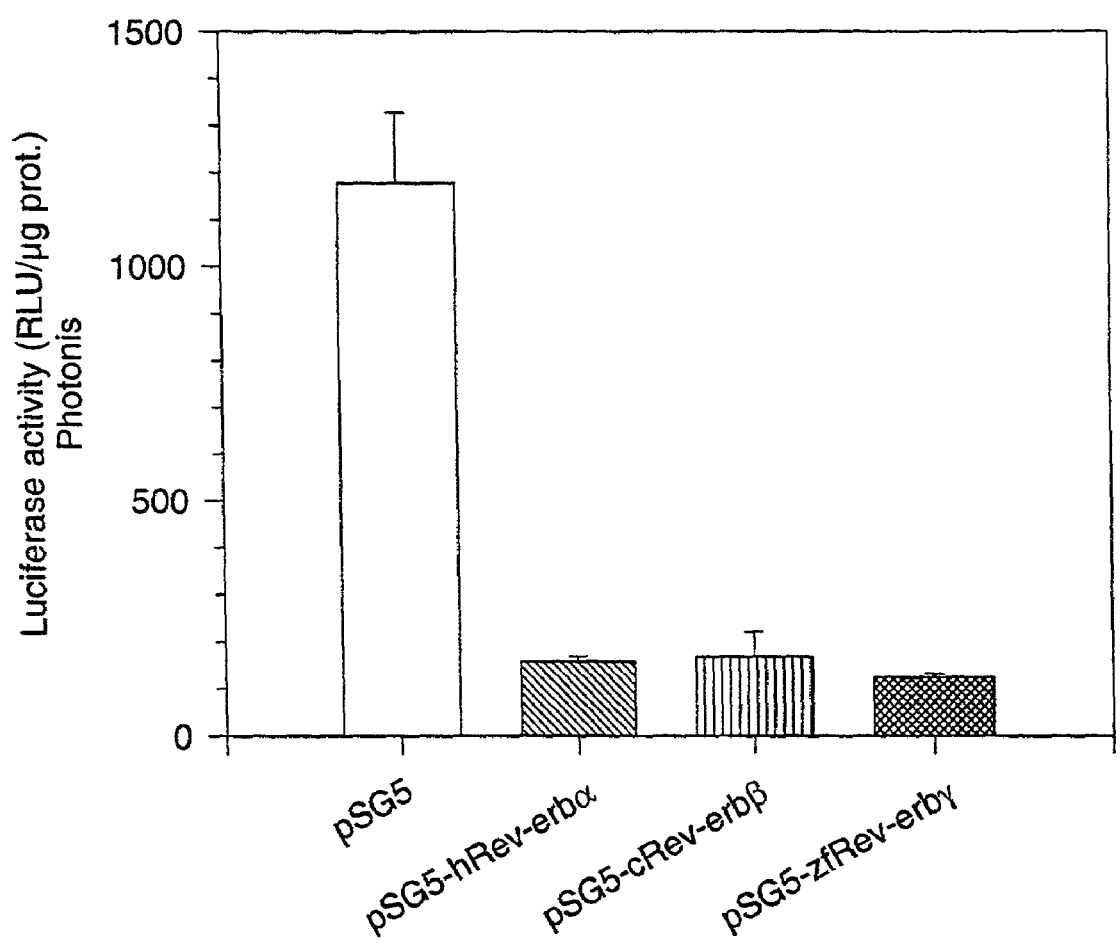
FIG. 9 shows, surprisingly, that the P and y Rev-erb isoforms also repress the activity of the construct −198/+24WTLuc+.

FIG. 9 shows, surprisingly, that the β and γ Rev-erb isoforms also repress the activity of the construct −198/+24WTLuc+.

6. Disruption of the Rev-erbα Gene in Rev-Erb KO Mice Affects the Hepatic Expression of apo C-III and the Plasma Levels of Apo C-III and Triglycerides In order to establish the physiological relevance of the observations made in vitro described above, the effect of the destruction by homologous recombination of the Rev-erbα gene in SV129XBalbC mice was evaluated on the blood parameters (plasma level of triglycerides and of apo C-III, lipid profile) and the accumulation of messenger RNAs coding for apo C-III in the liver of normal and transgenic animals.

a. Blood Parameters

Figure 10:
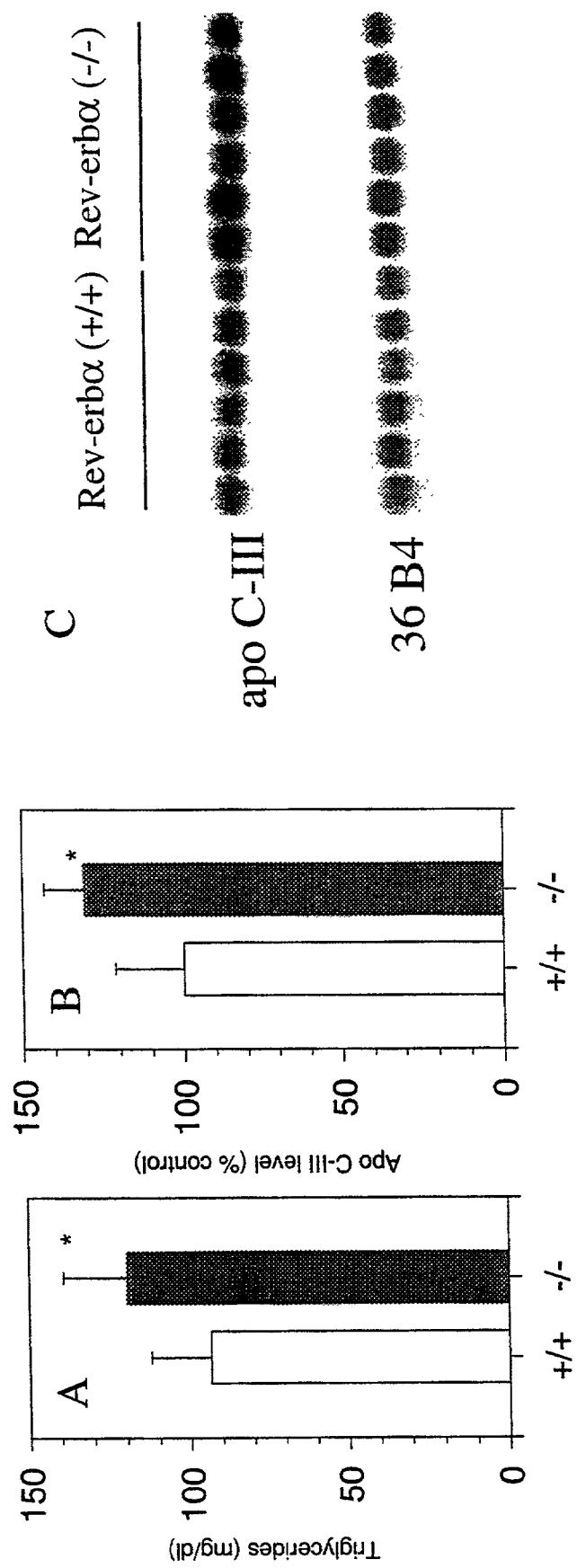
FIG. 10A shows that a significant increase in the serum triglyceride concentration was observed in Rev-erb KO mutant mice compared with normal mice.
FIG. 10B shows that the increased expression is associated with a significant increase in the level of apo C-III in the plasma.
FIG. 10C shows that the expression of the mRNA coding for apo C-III is increased in mice whose Rev-erba gene has been destroyed by homologous recombination.
Figure 11:
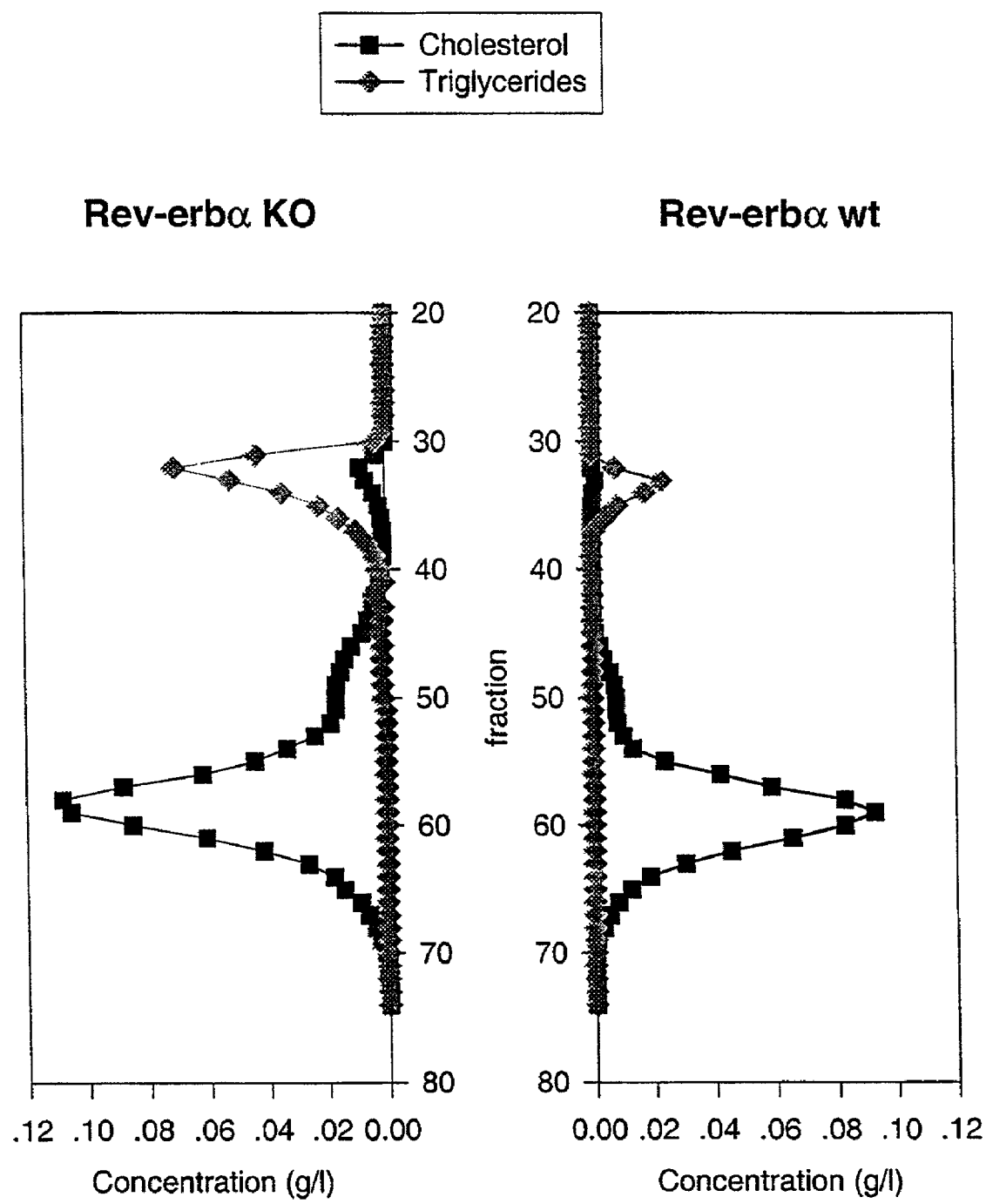
FIG. 11 demonstrates a large increase in triglycerides in the VLDL fraction, as measured by FIG. 12 characterizes a construct comprising three copies of the Rev-DR2 site present in the promoter for the human Rev-erba gene, which are cloned before the Tk promoter.

A significant increase (Mann-Whitney test, p<0.05) in the triglyceride concentration in the serum was observed in mutant mice compared with normal mice (FIG. 10A). The FPLC profile indicates a large increase in triglycerides in the VLDL fraction (FIG. 11).

b. Expression of the apo C-III Gene

Expression of the mRNA coding for apo C-III is increased in mice whose Rev-erbα gene has been destroyed by homologous recombination (FIG. 10C). This increased expression is associated with a significant increase (Mann-Whitney test, p<0.05) in the level of apo C-III in the plasma (FIG. 10B).

These results show that modifications in the expression of Rev-erb affect the hepatic expression of apo C-III and the levels of triglycerides and apo C-III in the plasma in mice: our observations made in vitro are physiologically relevant.

7. Relevance of the Screening Processes Proposed

Repression (FIGS. 1 to 5, 8 and 9) of the expression of the reporter gene cloned downstream of the promoter for the human apo C-III gene when the exogenous expression of hRev-erbα is artificially increased is the basis for the relevance of using this method to identify substances liable to modulate the activity of hRev-erbα.

Figure 12:
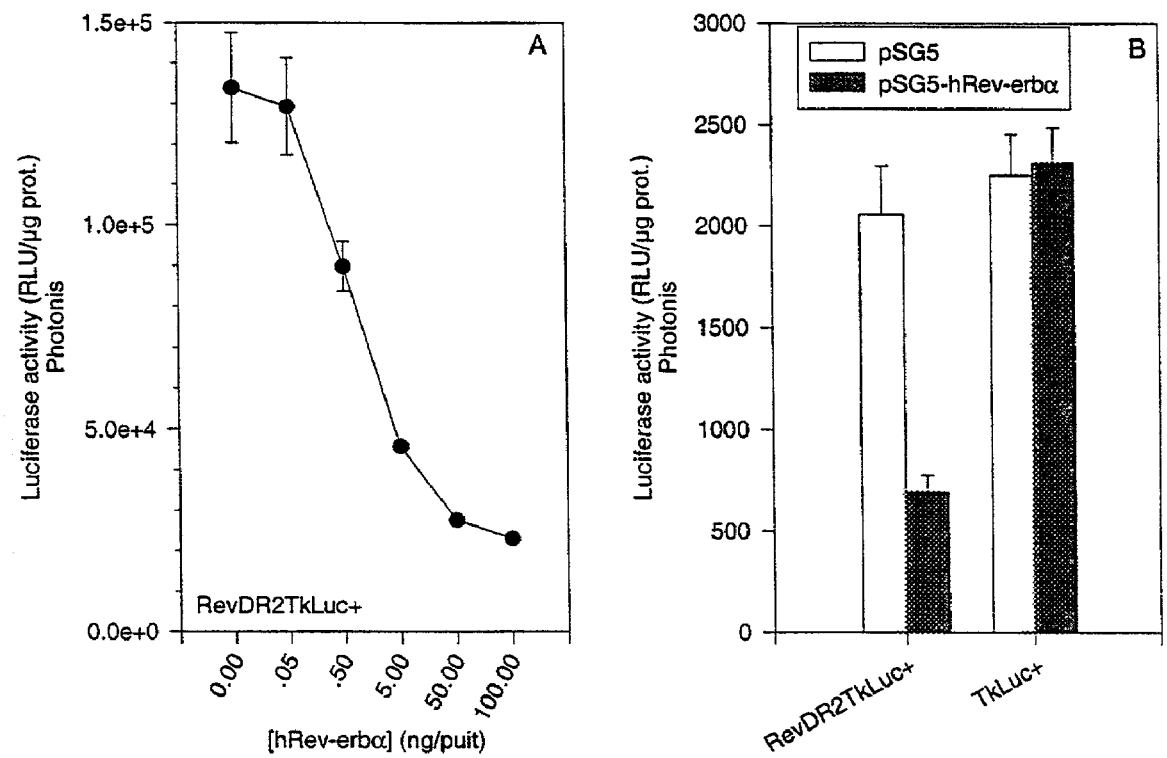

FIGS. 6 and 12 are the basis for the relevance of using isolated sites cloned upstream of the Tk promoter before a reporter gene in order to identify substances liable to modulate the activity of hRev-erbα. A construct comprising three copies of the Rev-DR2 site present in the promoter for the human Rev-erbα gene which are cloned before the Tk promoter has been characterized (FIG. 12). Its sensitivity to hRev-erbα is increased. This justifies its value for the screening of substances liable to modulate the activity of the native hRev-erbα nuclear receptor.

Figure 13:
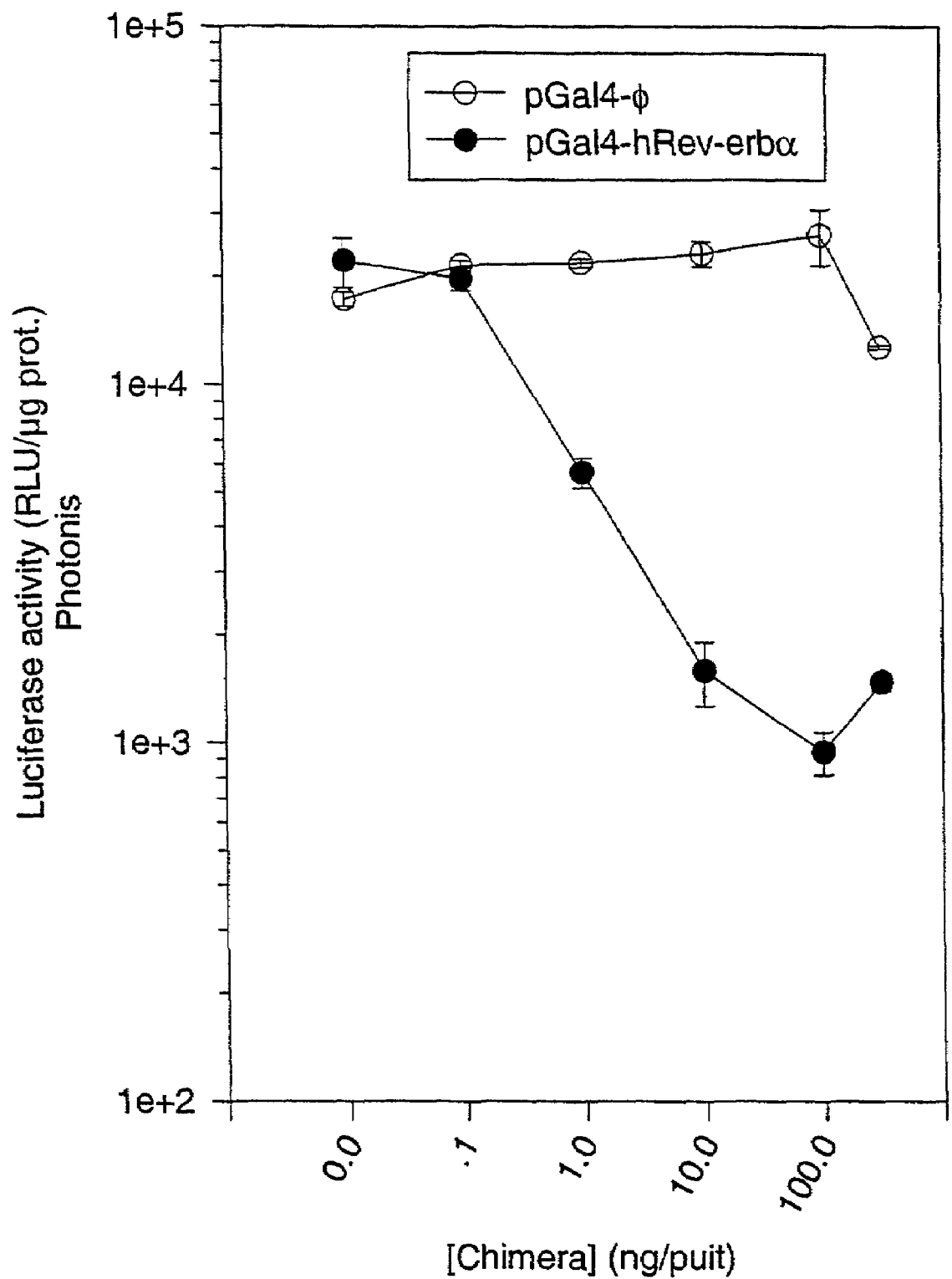
FIG. 13 depicts activity of the chimeras which combine the DNA binding domain of the yeast transcription factor Gal4 and the binding domain of the hRev-erba ligand and that of a reporter vector which comprises 5 copies of the Gal4 response element.

Lastly, FIG. 13 is the basis for the relevance of using chimeras which combine the DNA binding domain of the yeast transcription factor Gal4 and the binding domain of the hRev-erbα ligand and of a reporter vector which comprises 5 copies of the Gal4 response element in order to identify substances liable to modulate the activity of hRev-erbα.

BIBLIOGRAPHIC REFERENCES

1. M. D. Curry, W. J. McConathy, J. D. Fesmire and P. Alaupovic. 1980. Quantitative determination of human apolipoprotein C-III by electroimmunoassay. Biochim. Biophys. Acta. 617:503-513.
2. G. Schonfeld, P. I. Georges, J. Miller, P. Reilly and J. Witztum. 1979. Apolipoprotein C-II and C-III levels in hyperlipoproteinemia. Metabolism. 28:1001-1009.
3. J. Stocks, G. Holdsworth and D. J. Galton, 1979. Hypertriglyceridaemia associated with an abnormal triglyceride-rich lipoprotein carrying excess apolipoprotein C-III. Lancet. ii:667-671.
4. N.-A. Le, J. C. Gibson and H. N. Ginsberg. 1988. Independent regulation of plasma apolipoprotein C-II and C-III concentrations in very low density and high density lipoproteins: implications for the regulation of the catabolism of these lipoproteins. J. Lipid Res. 29:669-677.

5. G. Luc, C. Fievet, D. Arveiler, A. E. Evans, J.-M. Bard, F. Cambien, J.-C. Fruchart and P. Ducimetiere. 1996. Apolipoproteins C-III and E in apoB- and non-apoB-containing lipoproteins in two populations at contrasting risk for myocardial infarction: the ECTIM study. J. Lipid Res. 37:508-517.

6. C. L. Malmendier, J.-F. Lontie, C. Delcroix, D. Y. Dubois, T. Magot and L. De Roy. 1989. Apolipoproteins C-II and C-III metabolism in hypertriglyceridemic patients. Effect of a drastic triglyceride reduction by combined diet restriction and fenofibrate administration. Atherosclerosis. 77:139-149.

7. H. N. Ginsberg, N.-A. Le, I. J. Goldberg, J. C. Gibson, A. Rubinstein, P. Wang-Iverson, R. Norum and W. V. Brown. 1986. Apolipoprotein B metabolism in subjects with deficiency of apolipoproteins CIII and AI: evidence that apolipoprotein CIII inhibits catabolism of triglyceride-rich lipoproteins by lipoprotein lipase in vivo. J. Clin. Invest. 78:1287-1295.

8. M. Dammerman, L. A. Sandkuijl, J. L. Halaas, W. Chung and J. L. Breslow. 1993. An apolipoprotein CIII haplotype protective against hypertriglyceridemia is specified by promoter and 3' untranslated region polymorphisms. Proc. Natl. Acad. Sci. USA. 90:4562-4566.

9. A. Rees, C. C. Shoulders, J. Stocks, D. J. Galton and F. E. Baralle. 1983. DNA polymorphism adjacent to human apoprotein A-I gene: relation to hypertriglyceridemia. Lancet. i:444-446.

10. N. Maeda, H. Li, D. Lee, P. Oliver, S. H. Quarfordt and J. Osada. 1994. Targeted disruption of the apolipoprotein C-III gene in mice results in hypertriglyceridemia and protection from postprandial hypertriglyceridemia. J. Biol. Chem. 269:23610-23616.

11. Y. Ito, N. Azrolan, A. O'Connell, A. Walsh and J. L. Breslow. 1990. Hypertriglyceridemia as a result of human apo CIII gene expression in transgenic mice. Science. 249:790-793.

12. H. V. de Silva, S. J. Lauer, J. Wang, W. S. Simonet, K. H. Weisgraber, R. W. Mahley and J. M. Taylor. 1994. Overexpression of human apolipoprotein C-III in transgenic mice results in an accumulation of apolipoprotein B48 remnants that is corrected by excess apolipoprotein E. J. Biol. Chem. 269:2324-2335.

13. K. Aalto-Setälä, E. A. Fisher, X. Chen, T. Chajek-Shaul, T. Hayek, R. Zechner, A. Walsh, R. Ramakrishnan, H. N. Ginsberg and J. L. Breslow. 1992. Mechanism of hypertriglyceridemia in human apolipoprotein (apo) CIII transgenic mice. Diminished very low density lipoprotein fractional catabolic rate associated with increased apo CIII and reduced apo E on the particles. J. Clin. Invest. 90:1889-1900.

14. V. Clavey, S. Lestavel-Delattre, C. Copin, J. M. Bard and J. C. Fruchart. 1995. Modulation of lipoprotein B binding to the LDL receptor by exogenous lipids and apolipoproteins CI, CII, CIII, and E. Arterioscler. Throm. Vasc. Biol. 15:963-971.

15. K. Aalto-Setälä, P. H. Weinstock, C. L. Bisgaier, L. Wu, J. D. Smith and J. L. Breslow. 1996. Further characterization of the metabolic properties of triglyceride-rich lipoproteins from human and mouse apo C-III transgenic mice. J. Lipid Res. 37:1802-1811.

16. T. Ebara, R. Ramakrishnan, G. Steiner and N. S. Shachter. 1997. Chylomicronemia due to apolipoprotein CIII overexpression in apolipoprotein E-null mice. Apolipoprotein CIII-induced hypertriglyceridemia is not mediated by effects on apolipoprotein E. J. Clin. Invest. 99:2672-2681.

17. L. Masucci-Magoulas, I. Goldberg, C. Bisgaier, H. Serajuddin, O. Francone, J. Breslow, A. Tall. 1997. A mouse model with features of familial combined hyperlipidemia. Science. 275:391-394.

18. N. Miyajima, R. Horiuchi, Y. Shibuya, S.-i. Fukushige, K.-i. Matsubara, K. Toyoshima and T. Yamamoto, (1989) Two erbA homologs encoding proteins with different T3 binding capacities are transcribed from opposite DNA strands of the same genetic locus. Cell, 57, 31-39.

19. M. A. Lazar, R. A. Hodin, D. S. Darling and W. W. Chin. (1989) A novel member of the thyroid/steroid hormone receptor family is encoded by the opposite strand of the rat c-erbAa transcriptional unit. Mol. Cell. Biol., 9, 1128-1136.

20. B. Forman, J. Chen, B. Blumberg, S. A. Kliewer, R. Henshaw, E. S. Ong, R. Evans. Cross-talk among RORa1 and the Rev-erb family of nuclear receptor. Mol. Endocrinol. 8:1253.

21. B. Dumas, H. S. Harding, K. Choi, M. Lehman, M. Chung, M. A. Lazar, D. Moore. 1994. A new orphan member of the nuclear hormone receptor superfamily closely related to Rev-Erb. Mol. Endocrinol. 8:996.

22. S. Pena de Ortiz and G. A. Jamieson Jr. 1997 Molecular cloning and brain localization of HZF-2alpha, a new member of the rev-erb subfamily of orphan nuclear receptors. J. Neurobiol 32, 341-358.

23. E. Enmark, M. Kainu, M. Pelta Huikko, J. A. Gustafsson. 1994. Identification of a novel member of the nuclear receptor superfamily which is closely related to rev-erbA. Biochem. Biophys. Res. Commun. 204:49-56.

24. R. Retnakaran, G. Flock and V. Giguère, (1994) Identification of RVR, a novel orphan nuclear receptor that acts as a negative transcriptional regulator. Mol. Endocrinol., 8, 1234-1244.

25. E. Bonnelye, J. M. Vanacker, X. Desbiens, A. Begue, D. Stehelin and V. Laudet. (1994) Rev-erbB, a new member of the nuclear receptor family is expressed in the nervous system during chicken development. Cell Growth Differentiation, 5, 1357-1365.

26. A. Chawla and M. A. Lazar, (1993) Induction of Rev-erbAα, an orphan receptor encoded on the opposite strand of the a-thyroid hormone receptor gene, during adipocyte differentiation. J. Biol. Chem., 268, 16265-16269.

27. N. Vu-dac, S. Chopin-Delannoy, P. Gervois, E. Bonnelye, G. Martin, J. C. Fruchart, V. Laudet, B. Staels, 1998. The nuclear receptors peroxisome proliferator-activated receptor a and Rev-erbα mediate the species-specific regulation of apolipoprotein A-I expression by fibrates. J. Biol. Chem., 273(46), 25713-20.

28. H. P. Harding and M. A. Lazar 1993. The orphan receptor Rev-erbAα activates transcription via a novel response element. Mol. Cell. Biol 13:3113.

29. H. P. Harding and M. A. Lazar (1995). The monomer-binding orphan receptor Rev-erb represses transcription as a dimer on a novel direct repeat. Mol. Cell. Biol., 15, 4791-4802.

30.1. Dussault and V. Giguère (1997). Differential regulation of the N-myc proto-oncogene by RORa and RVR, two orphan members of the superfamily of nuclear homone receptors. Mol. Cell. Biol., 17, 1860-1867.

31. G. Adelmant, A. Bègue, D. Stéhelin and V. Laudet (1996). A functional Rev-erbα responsive element located in the human Rev-erbα promoter mediates a repressing activity. Proc. Natl. Acad. Sci. USA, 93, 3553-3558.

32. B. Luckow and G. Schütz. 1987. CAT constructions with multiple unique restriction sites for the functional analysis of eukaryotic promoters and regulatory elements. Nucl. Acids Res. 15:5490.
33. K. L. Nakamaye and F. Eckstein. 1986. Inhibition of restriction nuclease NciI cleavage by phosphorothiolate groups and its application to oligonucleotide-directed mutagenesis. Nucl. Acids Res. 14:9679-9698.
34. V. Giguère, M. Tini, G. Flock, E. Ong, R. M. Evans and G. Otulakowski (1994). Isoform-specific amino-terminal domains dictate DNA-binding properties of RORa, a novel family of orphan nuclear receptors. Genes Dev. 8, 538-553.
35. F. Chartier, J. P. Bossu, V. Laudet, J. C. Fruchart, B. Laine 1994. Cloning and sequencing of cDNAs encoding the human hepatocyte nuclear factor 4 indicate the presence of two isoforms in human liver. Gene. 147:269-272.
36. G. R. MacGregor and C. T. Caskey. 1989. Construction of plasmids that express *E. coli* b-galactosidase in mammalian cells. Nucl. Acids Res. 17:2365.
37. F. Ausubel, R. Brent, R. Kingston, D. Moore, J. Smith, G. Seidman, K. Struhl 1987. Current protocols in molecular biology, Greene Publishing-Wiley Interscience, New York.
38. B. Staels, N. Vu-Dac, V. A. Kosykh, R. Saladin, J. C. Fruchart, J. Dallongeville and J. Auwerx. 1995. Fibrates downregulate apolipoprotein C-III expression independent of induction of peroxisomal acyl coenzyme A oxidase. J. Clin. Invest. 95:705-712.
39. P. Masiakowski, R. Breathnach, J. Bloch, F. Gannon, A. Krust and P. Chambon. 1982. Cloning of cDNA sequences of hormone-regulated genes from MCF-7 human breast cancer cell line. Nucl. Acids Res. 10:7895-7903.
40. A. Dugaiczyk, J. Haron, E. Stone, O. Dennison, K. Rothblum, R. Schwartz. 1983. Cloning and sequencing of a deoxyribonucleic acid copy of glyceraldehyde-3-phosphate dehydrogenase messenger ribonucleic acid isolated from chicken muscle. Biochem. 29:1605-1613.
41. D. Cleveland, M. Lopata, R. MacDonald, N. Cowan, W. Rutter, M. Kirschner. 1980. Number and evolutionary conservation of alpha- and beta-tubulin and cytoplasmic beta- and gamma-actin genes using specific cloned cDNA probes. Cell 20:95-105 b-actin.
42. B. Staels and J. Auwerx. 1992. Perturbation of developmental gene expression in rat liver by fibric acid derivatives: lipoprotein lipase and alpha-fetoprotein as models. Development. 115:1035-1043.
43. J. M. Vanacker, V. Laudet, G. Adelmant, D. Stéhelin and J. Rommelaere (1993). Interconnection between thyroid hormone receptor signalling pathways and parvovirus cytotoxic functions. J. Virol., 67, 7668-7672.
44. N. Vu-Dac, K. Schoonjans, B. Laine, J. C. Fruchart, J. Auwerx and B. Staels (1994). Negative regulation of the human apolipoprotein A-I promoter by fibrates can be attenuated by the interaction of the peroxisome proliferator-activated receptor with its response element. J. Biol. Chem., 269, 31012-31018.
45. G. Krey, O. Braissant, F. LíHorset, E. Kalkhoven, M. Perroud, M. Parker, W. Wahli. 1997. Fatty acids, eicosanoids and hypolipidemic agents identified as ligands of peroxisome proliferator-activated receptors by coactivator-dependent receptor ligand assay. Mol. Endocrinol. 11:779-791.
46. M. G. Fried and D. M. Crothers (1983). CAP and RNA polymerase interactions with the lac promoter: binding stoichiometry and long range effects. Nucl. Acids Res., 11, 141-158.
47. J. A. A. Ladias, M. Hadzopoulou-Cladaras, D. Kardassis, P. Cardot, J. Cheng, V. Zannis and C. Cladaras (1992). Transcriptional regulation of human apolipoprotein genes apoB, apoCIII and apoAII by members of the steroid hormone receptor superfamily HNF-4, ARP-1, EAR-2 and EAR-3. J. Biol. Chem., 267, 15849-15860.
48. F. Moolten, 1994. Drug sensitivity (suicide) genes for selective cancer chemotherapy. Cancer Gene Ther. 1:125-134.
49. Webster et al., Cell, 52, 169-178.
50. I. Sadowski, J. Ma, S. Triezenberg, M. Ptashme, 1988. Gal4-VP16 is an unusually potent transcriptional activator. Nature 335, 563-564.
51. I. Zamir, H. Harding, G. Atkins, A. Horlein, C. Glass, M. Rosenfeld, M. Lazar, 1996. A nuclear receptor corepressor mediates transcriptional silencing by receptors with distinct repression domains. Mol. Cell. Biol. 16:5458-5465.
52. M. Downes, L. Burke, P. Bailey, G. Muscat, 1996. Two receptor interaction domains in the corepressor, N—COR/RIP13, are required for an efficient interaction with Rev-erbA alpha and RVR: physical association is dependent on the E region of the orphan receptors. Nucleic Acid Res. 24, 4379-4386.
53. M. Downes, A. J. Carozzi, G. E. Muscat, 1995. Constitutive expression of the orphan receptor, Rev-erbA alpha, inhibits muscle differentiation and abrogates the expression of the myoD gene family. Mol. Endocrinol., 12, 1666-78.
54. Q. Zhao, S. Khorasanizadeh, Y. Miyoshi, M. A. Lazar, F. Rastinejad, 1998. Structural elements of an orphan nuclear receptor-DNA complex. Mol. Cell, 1(6), 849-61.
55. A. Balsalobre, F. Damiola, U. Schiber, 1998. A serum shock induces circadian gene expression in mammalian tissue culture cells. Cell, 93(6), 929-37.
56. N. Vu-Dac, P. Gervois, I. P. Torra, J. C. Fruchart, V. Kosykh, T. Kooistra, H. M. Princen, J. Dallongeville, B. Staels. Retinoids increase human Apo C-III expression at the transcriptional level via the retinoid X receptor. Contribution to the hypertriglyceridemic action of retinoids. JCI, 1998, 102(3):623-32.
57. N. Vu-Dac, K. Schoonjans, V. Kosykh, J. Dallongeville, J. C. Fruchart, B. Staels, J. Auwerx. Fibrates increase human apolipoprotein A-II expression through activation of the peroxisome proliferator-activated receptor, JCI, 96, 741-750, 1995.
58. Webster et al., 1998. Cell. 52:169-178.
59. P. Gervois, S. Chopin-Delannoy, A. Fadel, G. Dubois, V. Kosykh, J. C. Fruchart, J. Najib, V. Laudet, B. Staels, 1999. Fibrates increase human Rev-erbα expression in liver via a novel peroxisome proliferator-activated receptor response element. Mol. Endocrinol. 13(3), 400-9.
60. R. Hertz, J. Bishara-Shieban, J. Bar-Tana, 1995. Mode of action of peroxisome proliferators as hypolipidemic drugs. Suppression of apolipoprotein C-III. J. Biol. Chem., 270 (22), 13470-5.
61. J. D. Fraser, V. Martinez, R. Stranley, M. R. Briggs, 1998. DNA binding and transcription activation specificity of hepatocyte nuclear factor 4. Nucleic Acids Res., 26(11), 2702-7.
62. M. Mietus-Synder, F. M. Sladek, G. S. Ginsburg, C. F. Kuo, J. A. Ladias, J. E. Darnell Jr., S. K. Karathanasis, 1992. Antagonism between apolipoprotein AI regulatory protein 1, Ear3/COUP-TF, and hepatocyte nuclear factor 4 modulates apolipoprotein CIII gene expression in liver and intestinal cells. Mol. Cell. Biol., 12(4), 1708-18.

We claim:

1. A method of screening for a substance which is useful in the treatment of a lipid metabolism dysfunction associated with apolipoprotein C-III, comprising
   contacting said substance with a human Rev-erb receptor protein (hRev-erb) or a protein which at least comprises the hRev-erb ligand binding site and the hRev-erb DNA binding site;
   providing a hRev-erb response element or a polynucleotide sequence onto which said Rev-erb receptor is capable of binding thereto; and
   detecting the transcriptional activity of a gene which is under the control of a promoter comprising said response element in the presence and absence of said test substance,
   wherein a decrease of said transcriptional activity of said gene in the presence of said test substance indicates that said test substance is useful in the treatment of said lipid metabolism dysfunction associated with apolipoprotein C-III.

2. The method according to claim 1, wherein the Rev-erb receptor is the hRev-erbα receptor and the Rev-erb receptor response element is the hRev-erba receptor response element.

3. A process for screening a substance which is useful in the treatment of a lipid metabolism dysfunction associated with apolipoprotein C-III, comprising
   placing a test substance in contact with a receptor of the human Rev-erb family hRev-erb) or a protein which at least comprises the hRev-erb ligand binding site and the hRev-erb DNA binding site,
   providing a human Rev-erb receptor response element or a polynucleotide sequence onto which said hRev-erb is capable of binding thereto,
   providing a nuclear factor which is capable of functionally coupling the Rev-erb to an RNA-polymerase complex, and
   measuring:
   (a) (i) the binding of said test substance to the Rev-erb receptor or
       (ii) the binding of a test substance-hRev-erb receptor complex to said hRev-erb response element or to a nuclear factor capable of functionally coupling said hRev-erb to the RNA polymerase complex,
   and
   (b) optionally detecting the decrease of transcriptional activity of a gene which is under the control of a promoter comprising the hRev-erb response element.

4. A method for the characterization or testing of the mechanism of action of a substance having anti-atherosclerotic properties comprising
   placing said substance in contact with a receptor of the Rev-erb family (hRev-erb) or a protein which at least comprises the hRev-erb ligand binding site and the hRev-erb DNA binding site,
   providing a human Rev-erb receptor response element or a polynucleotide sequence onto which said hRev-erb receptor is capable of binding thereto,
   providing a nuclear factor which is capable of functionally coupling said hRev-erb to an RNA-polymerase complex, and measuring:
   (a) (i) the binding of said substance to the Rev-erb receptor or
       (ii) the binding of a test substance-hRev-erb receptor complex to said hRev-erb response element or to a nuclear factor capable of functionally coupling said hRev-erb to the RNA polymerase complex,
   (b) detecting the decrease of transcriptional activity of a gene which is under the control of a promoter comprising the hRev-erb response element,
   and
   (c) determining the mechanism of action of said anti-atherosclerotic compound based on assays (a) or (b).

5. The method according to claim 3, wherein said gene is apolipoprotein C-III (apo C-III).

6. The method according to claim 5 wherein a reduction in the transcriptional activity of said apolipoprotein C-III (apo C-III) in presence of said test compound indicates that said test compound is useful in the treatment of said lipid metabolism dysfunction associated with apolipoprotein C-III.

7. The method according to claim 4, wherein said gene is apolipoprotein C-III (apo C-III).

8. The method according to claim 7 wherein a reduction in the transcriptional activity of said apolipoprotein C-III (apo C-III) in presence of said compound indicates that said compound has anti-atherosclerotic property.

9. The method according to claim 1, wherein the hRev-erb receptor protein is a chimeric protein comprising said hRev-erb receptor protein.

10. The method according to claim 9, wherein the Rev-erb receptor protein is a chimeric protein comprising Rev-erb ligand binding site and maltose-binding-protein or a chimeric protein comprising Rev-erb ligand binding site and glutathione-S-transferase.

\* \* \* \* \*

SEQUENCE LISTING

<160> NUMBER OF SEQ ID NOS: 30

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caggcaggag ggttcatgtg tgttttatat catctcc                               37

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccctcatctc cactggtgag ctcgtg                                           26

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatccgataa aacaggtcag aa                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcttctga cctgttttat cg                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatccgataa aacacacatg aa                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gatcttcatg tgtgttttat cg                                          22

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatcccgctg ggcaaaggtc acctgca                                     27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatctgcagg tgacctttgc ccagcgc                                     27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatcctcacc tgctgaccag tggaga                                      26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatctctcca ctggtcagca ggtgag                                      26

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatgggatcc gccagggttt tcccagtcac gac                              33

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```
tcgccaagct tctcgtgatc tgcggca                                        27

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tatgcagttg ctctccagcg gttccatctt cc                                  32

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgactctaga agatcttgcc ccgcccagcg                                     30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gatccggaaa agtgtgtcac tggggcacga                                     30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatctcgtgc cccagtgaca cacttttccg                                     30

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatcctcatc tccactggtc agcaggtgac ctttgc                              36

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatcggcaaa ggtcacctgc tgaccagtgg agatgag                             37

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatctgatat aaaacaggtc agaaccctc                               29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatcgagggt tctgacctgt tttatatca                               29

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gatcgatata aaacaggcag gaaccctc                                28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatcgagggt tcctgcctgt tttatatc                                28

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatcctcagt gcctgctgcc ctggagatga tataa                        35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gatcttatat catctccagg gcagcaggca ctgag                        35

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gatccttgcc cagcgccctg ggtcctcagt gcctga         36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
gatctcaggc actgaggacc cagggcgctg ggcaag         36

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gatctcatct ccactggtca gcaggtgacc tttgcccagc gccctg         46

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
gatccagggc gctgggcaaa ggtcacctgc tgaccagtgg agatga         46

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
ggagatgata taaaacacac atgaaccctc ctgcctg         37

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(4)

-continued

```
<223> OTHER INFORMATION: a, c, t, g, unknown or other

<400> SEQUENCE: 30
wawntrggtc a                                                              11
```